(12) United States Patent
Tillekeratne et al.

(10) Patent No.: US 8,435,983 B2
(45) Date of Patent: May 7, 2013

(54) CONFORMATIONALLY RESTRAINED EPOTHILONE ANALOGUES AS ANTI-LEUKEMIC AGENTS

(75) Inventors: Viranga Tillekeratne, Toledo, OH (US); Richard A. Hudson, Toledo, OH (US); Mamoun Alhamadsheh, Toledo, OH (US)

(73) Assignee: The University of Toledo, Toledo, OH (US)

( * ) Notice: Subject to any disclaimer, the term of this patent is extended or adjusted under 35 U.S.C. 154(b) by 420 days.

(21) Appl. No.: 12/532,829

(22) PCT Filed: Mar. 20, 2008

(86) PCT No.: PCT/US2008/003638
§ 371 (c)(1),
(2), (4) Date: Mar. 9, 2010

(87) PCT Pub. No.: WO2008/118327
PCT Pub. Date: Oct. 2, 2008

(65) Prior Publication Data
US 2010/0324094 A1      Dec. 23, 2010

Related U.S. Application Data

(60) Provisional application No. 60/919,804, filed on Mar. 23, 2007.

(51) Int. Cl.
| | | |
|---|---|---|
| *C07D 401/00* | (2006.01) | |
| *C07D 405/00* | (2006.01) | |
| *C07D 403/00* | (2006.01) | |
| *C07D 217/00* | (2006.01) | |
| *A01N 43/40* | (2006.01) | |
| *A61K 31/445* | (2006.01) | |
| *A61K 31/55* | (2006.01) | |

(52) U.S. Cl.
USPC ........ 514/228.2; 514/323; 540/602; 544/373; 546/147; 546/200; 548/517

(58) Field of Classification Search .......................... None
See application file for complete search history.

(56) References Cited

U.S. PATENT DOCUMENTS

| | | |
|---|---|---|
| 6,284,781 B1 | 9/2001 | Danishefsky et al. |
| 6,380,394 B1 | 4/2002 | Nicolaou et al. |
| 6,660,758 B1 | 12/2003 | Nicolaou et al. |
| 7,173,137 B2 | 2/2007 | Nicolaou et al. |
| 2003/0004338 A1 | 1/2003 | Li et al. |
| 2003/0176368 A1 | 9/2003 | Danishefsky et al. |
| 2004/0018598 A1 | 1/2004 | Santi et al. |
| 2004/0127432 A1 | 7/2004 | Nicolaou et al. |
| 2005/0033059 A1 | 2/2005 | Danishefsky et al. |
| 2005/0043376 A1 | 2/2005 | Danishefsky et al. |
| 2009/0258904 A1 | 10/2009 | Tillekeratne et al. |

FOREIGN PATENT DOCUMENTS

| | | |
|---|---|---|
| WO | 2006017761 A2 | 2/2006 |
| WO | 2007015929 A2 | 2/2007 |

OTHER PUBLICATIONS

PCT International Search Report and the Written Opinion of the International Searching Authority, International Application No. PCT/US2006/28169, International filing date Jul. 20, 2006, dated Sep. 27, 2007.
PCT International Preliminary Report on Patentability, International Application No. PCT/US2006/028169, International filing date Jul. 20, 2006, dated Feb. 7, 2008.
PCT International Search Report, International Application No. PCT/US2008/03638, International filing dated Mar. 20, 2008, dated Jun. 30, 2008.
PCT International Search Report and the Written Opinion of the International Searching Authority, International Application No. PCT/US2008/03638, International filed Mar. 20, 2008, dated Jun. 30, 2008.
International Preliminary Report on Patentability, International Application No. PCT/US2008/003638, International filed Mar. 20, 2008, dated Oct. 8, 2009.
sciFinder Scholar, search results; Sep. 12, 2004; pp. 1-54.

*Primary Examiner* — Anna Pagonakis
(74) *Attorney, Agent, or Firm* — MacMillan, Sobanski & Todd, LLC

(57) ABSTRACT

A method for synthesizing anti-leukemic epothilone analogues includes rigidifying a region between the macrolactone ring and the aromatic side-chain. The anti-leukemic compositions are non-naturally occurring epothilone analogue that are rigidified between the macrolactone ring and the aromatic side-chain.

6 Claims, 13 Drawing Sheets

R = H epothilone A
R = CH₃ epothilone B

R = H epothilone C
R = CH₃ epothilone D

1a

1b

*Scheme 1.* Retrosynthetic analysis of the designed epothilones.

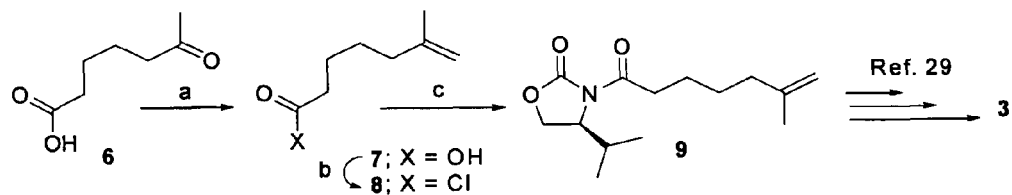

Scheme 2. Synthesis of aldehyde 3. Reagents and conditions: a) MeP$^+$(Ph)$_3$Br$^-$, n-BuLi, DMSO/THF, RT, 48 h, 78%; b) (COCl)$_2$, benzene; c) (S)-4-isopropyl-2-oxazolidonone, n-BuLi, THF, -78°C ⟶ 0°C, 96%.

Fig. 4

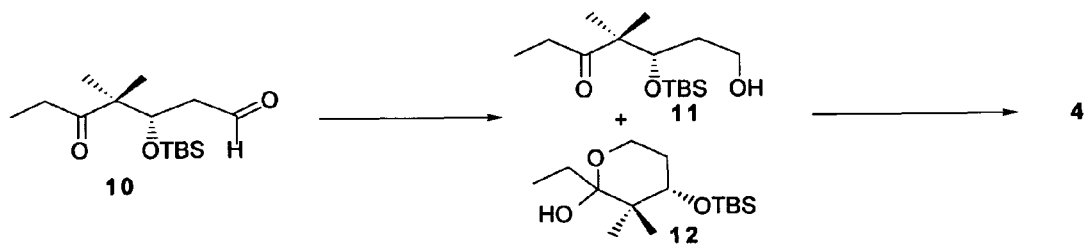

Scheme 3. Synthesis of intermediate 4. Reagents and conditons: a) NaBH$_4$, CH$_2$Cl$_2$, EtOH, -78°C; b) TBSCl, imidazole, CH$_2$Cl$_2$, 0°C ⟶ RT, 16 h, 81% (2 steps). TBSCl = tert-butyldimethylsilyl chloride

Fig. 5

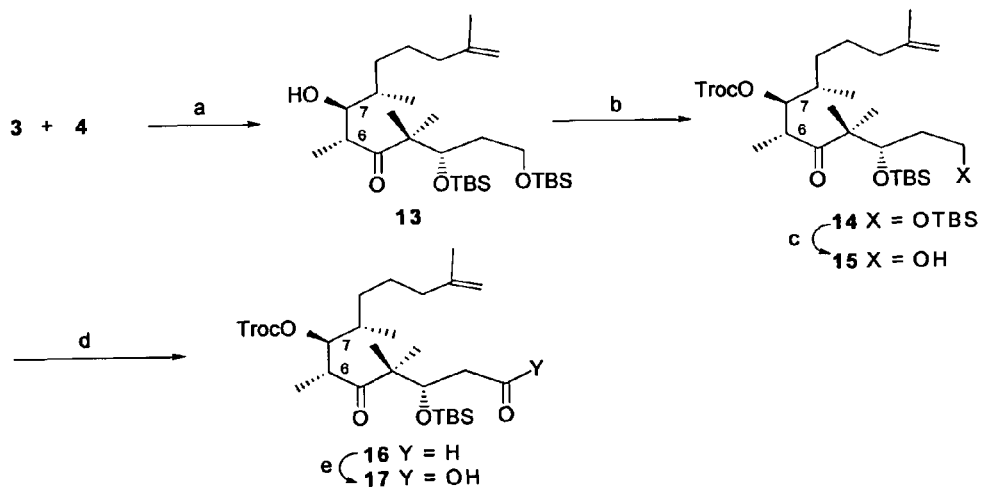

Scheme 4. Synthesis of 17. Reagents and conditions: a) LDA, THF, -78°C, 83%; b) TrocCl, pyridine, CH$_2$Cl$_2$, 0°C, 1 h, 93%; c) CSA, CH$_2$Cl$_2$/MeOH, 0°C, 7 h, 87%; d) DMP, CH$_2$Cl$_2$, RT, 15 min; e) NaClO$_2$, NaH$_2$PO$_4$, H$_2$O/t-BuOH, 2-methyl-2-butene, RT, 1 h, 90% (2 steps). LDA = lithium diisopropylamide, DMP = Dess-Martin periodinane

Fig. 6

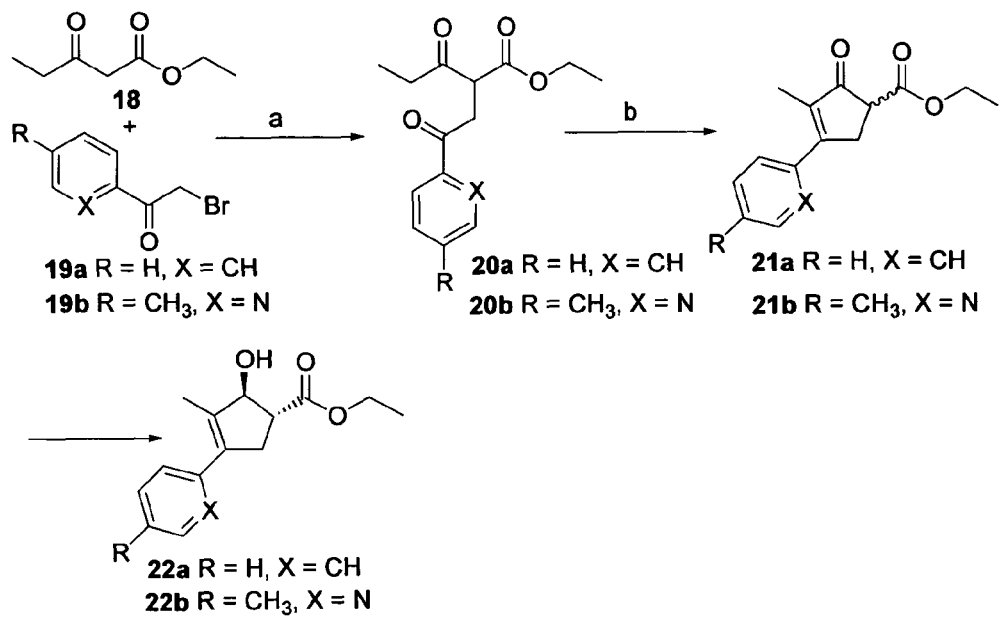

Scheme 5. Synthesis of 21a and 21b. Reagents and conditions: a) NaH, THF, 0°C, 82% (20a), 76% (20b); b) NaOH, anhy. EtOH, 78% (21a), 73% (21b).

Fig. 7

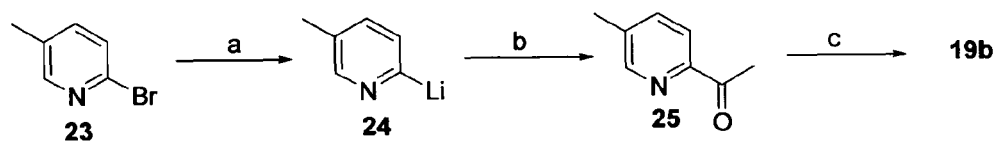

Scheme 6. Synthesis of α-bromoketone 19b. Reagents and conditions: a) n-BuLi, ether, -78°C; b) N,N-dimethylacetamide, ether, -78°C, 72% (2 steps); c) polymer-supported Amberlyst A26-Br$_3^-$, THF, 91%.

Fig. 8

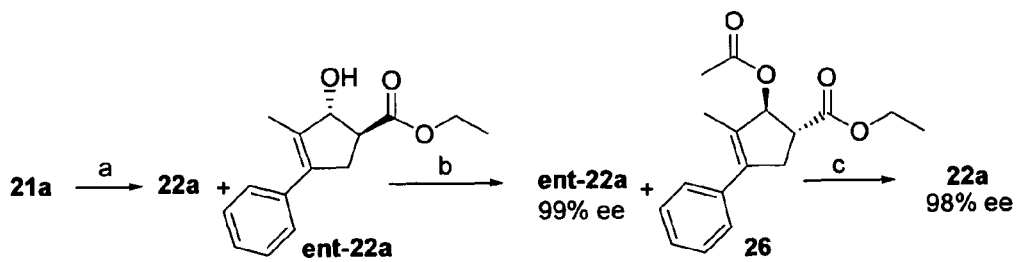

Scheme 7. Synthesis of the trans β-hydroxyester 22a. Reagents and conditions: a) Zn(BH$_4$)$_2$/ether, 4°C, 75%; b) PS-D lipase, vinyl acetate, 4 Å MS, pentane, RT, 4 days, 48% (ent-22a), 49% (26); c) anhy. K$_2$CO$_3$, anhy. EtOH, RT, 12 h, 92%.

Fig. 9

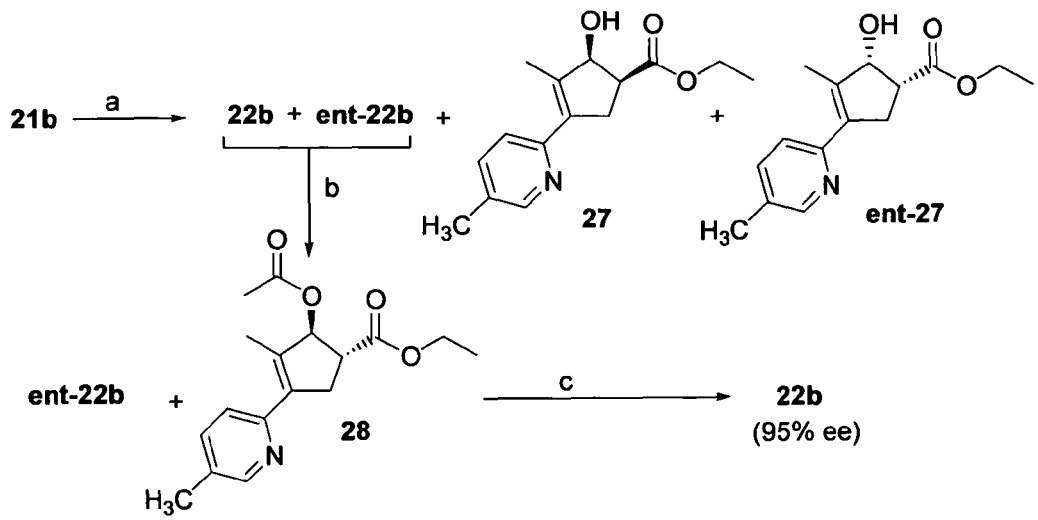

Scheme 8. Synthesis of the *trans* β-hydroxyester 22b. Reagents and conditions:
a) i. TFA, CH$_2$Cl$_2$, solvent evaporated, ii. residue in MeOH, NaBH$_4$, 0°C, 30 min;
b) PS-D lipase, vinyl acetate, 4 Å MS, pentane, RT, 3 days, 48% ( ent-22b), 49% (28);
c) anhy. K$_2$CO$_3$, anhy. EtOH, RT, 12 h, 94%. TFA = trifluoroacetic acid.

Fig. 10

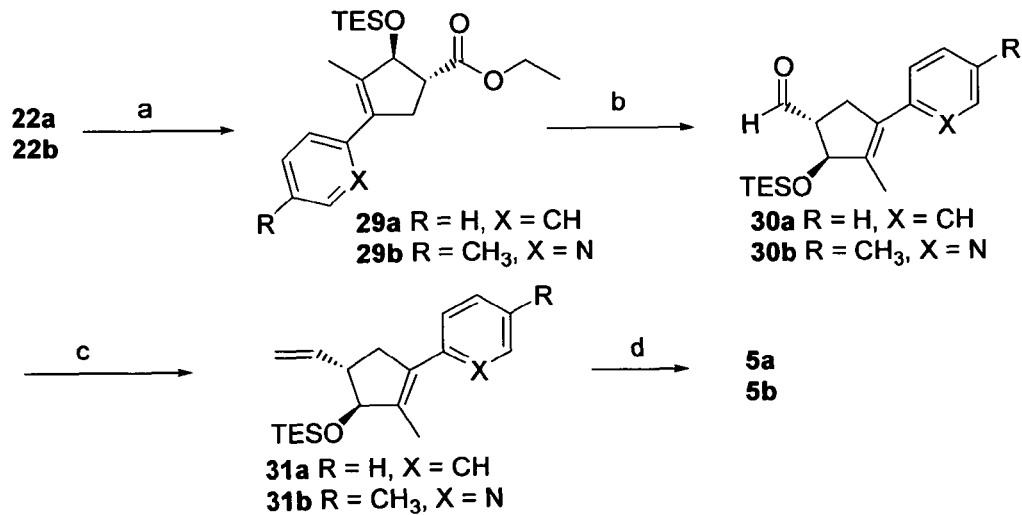

Scheme 9. Synthesis of 5a and 5b. Reagents and conditions: a) TESCl, imidazole, CH$_2$Cl$_2$, 0°C, 2 h, 93% (29a), 92% (29b); b) DIBAL-H, toluene, -78°C, 1 h; c) MeP(Ph)$_3$Br$^-$, n-BuLi, THF, 0°C, 30 min, 71% (31a), 73% (31b); d) TBAF, THF, 0°C, 30 min, 80% (5a), 83% (5b). TESCl = triethylsilyl chloride, DIBAL-H = diisobutylaluminum hydride, TBAF = tetrabutylammonium fluoride.

Fig. 11

Scheme 10. Synthesis of epothilone 1a. Reagents and conditions: a) DCC, DMAP, CH₂Cl₂, 0°C (15 min), RT (16 h), 64%; b) Zn, NH₄Cl, anhy. EtOH, RT, 45 min; c) TAS-F, DMF, 2 days, 62% (2 steps); d) CH₂Cl₂, 50°C, 16 h, 50% (Z + E). DCC = 1,3-dicyclohexylcarbodiimide, DMAP = 4-dimethylaminopyridine, TAS-F = tris(dimethylamino)sulfur (trimethylsilyl)difluoride.

Scheme 11. Synthesis of epothilone 1b. Reagents and conditions: a) DCC, DMAP, CH$_2$Cl$_2$, 0°C (15 min), RT (16 h), 85%; b) TAS-F, DMF, 2 days; c) Zn, NH$_4$Cl, anhy. EtOH, RT, 45 min, 62% (2 steps); d) CH$_2$Cl$_2$, 50°C, 16 h, 55%.

CONFORMATIONALLY RESTRAINED EPOTHILONE ANALOGUES AS ANTI-LEUKEMIC AGENTS

The present invention claims the benefit of the PCT/US2008/003638 filed Mar. 20, 2008, which claims priority to the provisional patent application Ser. No. 60/919,804 filed Mar. 23, 2007.

This invention was not made with any Government support and the Government has no rights in this invention.

BACKGROUND OF THE INVENTION

Microtubules are essential components of the cytoskeleton. Agents that disrupt microtubule dynamics within the cell have the potential of arresting cell division and cell proliferation (anti-mitotic agents) and consequentially, acting as anticancer agents. Two types of such agents have been identified. One class inhibits the polymerization of α- and β-tubulin, to microtubules, and is exemplified by compounds such as colchicines and vinca alkaloids, some of which are clinically used anticancer drugs. In contrast, the second class of anti-mitotic agents accelerates the polymerization of tubulin to microtubules and stabilizes them, thus inhibiting their depolymerization, an essential process during cell division. This second class is commonly referred to as microtubule-stabilizing agents. Paclitaxel (Taxol), initially isolated from the Pacific Yew tree, *Taxus bravifolia*, was the first of its kind reported and is already in clinical use.

A number of limitations are encountered in the clinical use of paclitaxel. One major limitation is its susceptibility to multiple drug-resistance. Several other compounds possessing the same mechanism of action as paclitaxel have been reported since then. Epothilones, originally isolated from the myxobacterium *Sorangium cellulosum*, constitute one such class. They are competitive inhibitors of paclitaxel binding and have been shown to compete for the same or overlapping binding sites on microtubules. From the point of view of anticancer properties, they possess a number of advantages over paclitaxel. Prominent among them is their activity against multiple drug resistant cell lines, which are resistant to paclitaxel.

Extensive studies on structure-activity relationship (SAR) of epothilones have been reported. Many analogues have been synthesized with the aim of improving the pharmacological profile of epothilones. A few epothilone analogues are in various stages of clinical development.

Despite the promising therapeutic utility of the epothilones, it would be desirable to investigate additional analogues as well as additional synthetic methodologies for the synthesis of existing epothilones, and analogues thereof, as well as novel analogues thereof.

In particular, given the interest in the therapeutic utility of this class of compounds, it would also be desirable to develop methodologies capable of providing significant quantities of any epothilones, or those described herein, for clinical trials and for large-scale preparation.

Due to the increasing interest in epothilones as anti-cancer agents, novel analogues of these compounds are needed and desired to more fully develop their therapeutic potential. The present invention fulfils this need.

SUMMARY OF THE INVENTION

Described herein is a method for screening a conformationally restrained epothilone compound for activity against a leukemic disease, which comprises contacting mammalian cells with the conformationally restrained epothilone compound and detecting an increased level of activity of the conformationally restrained epothilone compound relative to a control. The cell line can be one that is established from a subject having a leukemic disease. In certain embodiments, the cell line comprises at least one of CCRF-CEM and SR leukemia cell lines.

In another aspect, there is provided a method of evaluating a response by a mammalian subject to a leukemia inhibiting compound which comprises measuring the level of growth inhibitory activity in cells of the subject and comparing it to the level prior to administration of the inhibiting compound.

Also, provided is a method of evaluating a response by a mammalian subject to a conformationally restrained epothilone anti-leukemic agent which comprises measuring the level of growth inhibitory activity in cells of the subject and comparing it to the level prior to administration of the conformationally restrained epothilone anti-leukemic agent.

Further provided is a method of diagnosing a leukemic disease susceptible to treatment with conformationally restrained epothilone anti-leukemic compounds in a mammalian subject, which comprises measuring in cells of the subject that exhibiting the leukemic disease an increased level of growth inhibitory activity compared to the level prior to administration of the conformationally restrained epothilone anti-leukemic compound.

Still further provided is a method of diagnosing a leukemic disease susceptible to treatment with a conformationally restrained epothilone agent in a mammalian subject, which comprises measuring in cells of the subject that exhibiting the leukemic disease at increased level of growth inhibitory activity compared to the level prior to administration of the conformationally restrained epothilone agent.

In another aspect, there is provided herein a method of treating a leukemic disease in a mammalian subject, which comprises measuring the level of growth inhibitory activity in cells from the subject that exhibits the leukemic disease and administering a conformationally restrained epothilone compound to the subject if the level of growth inhibitory activity is lower than that exhibited by normal cells of the same type.

The method of treating a leukemic disease in a mammalian subject can include measuring the level of growth inhibitory activity in cells from the subject that exhibits the leukemic disease and administering a conformationally restrained epothilone agent to the subject if the level of growth inhibitory activity is lower than that exhibited by normal cells of the same type.

In yet another aspect, there is provided herein the use of a conformationally restrained epothilone compound as a biomarker for a leukemic disease.

Various objects and advantages of this invention will become apparent to those skilled in the art from the following detailed description of the preferred embodiment, when read in light of the accompanying drawings.

BRIEF DESCRIPTION OF THE DRAWINGS

FIG. 4 shows the synthesis of aldehyde 3 (Scheme 2).

FIG. 5 shows the synthesis of intermediate 4 (Scheme 3).

FIG. 6 shows synthesis of intermediate 17 (Scheme 4).

FIG. 7 shows synthesis of intermediate 21a and 21b (Scheme 5).

FIG. 8 shows synthesis of intermediate 19b (Scheme 6).

FIG. 9 shows synthesis of intermediate 22a (Scheme 7).

FIG. 10 shows synthesis of intermediate 22b (Scheme 8).

FIG. 11 shows synthesis of intermediate 5a and 5b (Scheme 9).

FIG. 12 shows the NOE correlations of (1S,5S)-2-methyl-3-phenyl-5-vinylcyclopent-2-enol 5a.

DETAILED DESCRIPTION OF THE INVENTION

Figure 1:
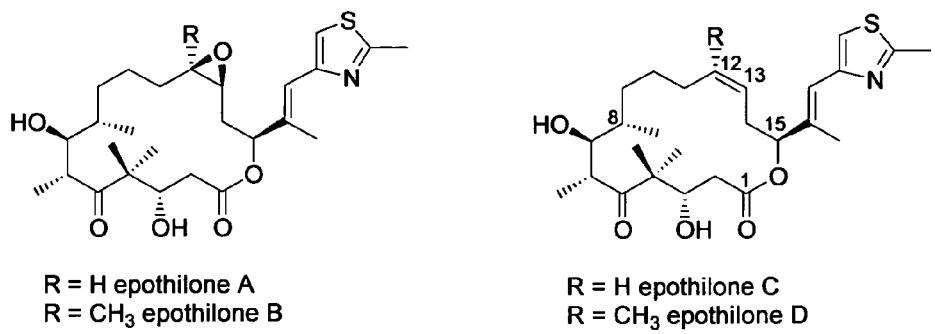
FIG. 1 shows naturally occurring epothilones.

Described herein are epothilone compounds that are useful for the treatment of cancer and other conditions characterized by undesirable cellular proliferation.

In another aspect, methods for preparing the compounds are provided. In one embodiment, certain of the compounds are prepared by total synthesis.

In another aspect, formulations comprising one or more of these compounds are provided. In one embodiment, the compounds constitute the active principle of the formulation. In another embodiment, the compounds are combined with other active compounds, such as cytotoxic agents and synergists.

In another aspect, methods for treating a disease or condition with the compounds are provided. In one embodiment, the compounds are used for treating a disease or condition characterized by cellular hyperproliferation in a subject. In one embodiment, the disease is cancer, including but not limited to cancers of the head and neck, liver or biliary tract, intestine, ovary, lung, central nervous system, lymphatic system, or sarcomas. In another embodiment, the condition includes cellular hyperproliferative disorders.

Statements regarding the definitions of terms used herein are listed below. The definitions apply to the terms as they are used throughout this specification, unless otherwise limited in specific instances, either individually or as part of a larger group.

Unless stereochemistry is specifically indicated, all stereoisomers of the compounds are included, as pure compounds, as well as mixtures thereof.

Some of the crystalline forms for the compounds may exist as polymorphs and as such are included. In addition, some of the compounds may form solvates with water (i.e., hydrates) or common organic solvents.

Protected forms of the compounds are included. A variety of protecting groups are disclosed; for example, a hydroxy protected form of the compounds are those where at least one of the hydroxyl groups is protected by a hydroxy protecting group.

In another aspect, prodrugs of the compounds are included. In general, such prodrugs are functional derivatives of the compounds that are readily convertible in vivo into the required compound. Thus, in the methods of treatment, the term "administering" includes the treatment of the various disorders described with the compound specifically disclosed or with a compound which may not be specifically disclosed, but which converts to the specified compound in vivo after administration to a subject in need thereof. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable salt" is a salt of a compound. Suitable pharmaceutically acceptable salts of the compounds include acid addition salts which may, for example, be formed by mixing a solution of the compound with a solution of a pharmaceutically acceptable acid.

The term "pharmaceutically acceptable carrier" is a medium that is used to prepare a desired dosage form of the compound. A pharmaceutically acceptable carrier includes solvents, diluents, or other liquid vehicle; dispersion or suspension aids; surface active agents; isotonic agents; thickening or emulsifying agents, preservatives; solid binders; lubricants and the like.

The term "purified," as used in reference to a compound means that the compound is in a preparation in which the compound forms a major component of the composition, such as constituting about 50%, about 60%, about 70%, about 80%, about 90%, about 95% or more by weight of the components in the composition.

Pharmaceutical preparations can include at least one of the compounds as described above and herein, or a pharmaceutically acceptable derivative thereof, which compounds are capable of inhibiting the growth of or killing cancer cells, and, in certain embodiments, are capable of inhibiting the growth of or killing multidrug resistant cancer cells. In certain embodiments, the pharmaceutical preparation also comprises a solubilizing or emulsifying agent.

In yet another aspect, methods for inhibiting tumor growth and/or tumor metastasis are provided. In certain embodiments, the method includes treating cancers by inhibiting tumor growth and/or tumor metastasis for tumors of multidrug resistant cancer cells. The method involves the administration of a therapeutically effective amount of the compound or a pharmaceutically acceptable derivative thereof to a subject (including, but not limited to a human or animal) in need of it. In certain embodiments, specifically for treating cancers comprising multidrug resistant cancer cells, the therapeutically effective amount is an amount sufficient to kill or inhibit the growth of multidrug resistant cancer cell lines. In certain embodiments, the compounds are useful for the treatment of solid tumors.

It will be appreciated by one of ordinary skill in the art that asymmetric centers may exist in the compounds. Thus, the compounds and pharmaceutical compositions thereof may be in the form of an individual enantiomer, diastereomer or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures described herein encompass those structures in which double bonds are (Z) or (E).

It will be appreciated that the compounds, as described herein, may be substituted with any number of substituents or functional moieties. In general, the term "substituted" whether preceded by the term "optionally" or not, and substituents contained in formulas refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of explanation herein, heteroatoms such as nitrogen may have hydrogen substituents and/or any permissible substituents of organic compounds described herein which satisfy the valencies of the heteroatoms.

Furthermore, there not any intention to be limited in any manner by the permissible substituents of organic compounds. Combinations of substituents and variables envisioned are preferably those that result in the formation of stable compounds useful in the treatment, for example, of proliferative disorders, including, but not limited to cancer.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Also provided are pharmaceutical agents that are based on pharmaceutically compatible compounds, i.e., compounds that are nontoxic in the doses used, optionally together with commonly used adjuvants and vehicles.

A composition generally comprises a compound and a pharmaceutically acceptable carrier. The compound may be in free form or where appropriate as pharmaceutically acceptable derivatives such as prodrugs, and salts and esters of the compound.

The composition may be in any suitable form such as solid, semisolid, or liquid form. In general, the pharmaceutical preparation will contain one or more of the compounds as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, cornstarch, keratin, colloidal silica, potato starch, urea, and other carriers suitable for use in manufacturing preparations, in solid, semi-solid, or liquefied form. In addition, auxiliary stabilizing, thickening, and coloring agents and perfumes may be used.

The amount of active ingredient that may be combined with the carrier materials to produce a single dosage form will vary depending upon the subject treated and the particular mode of administration. For example, a formulation for intravenous use comprises an amount of the compound ranging from about 1 mg/mL to about 25 mg/mL, preferably from about 5 mg/mL to 15 mg/mL, and more preferably about 10 mg/mL. Intravenous formulations are typically diluted between about 2 fold and about 30 fold with normal saline or 5% dextrose solution prior to use.

Methods of Treatment

In a particular embodiment, the compounds are used to treat leukemic cancers.

The method comprises administering a therapeutically effective amount of a compound to a subject suffering from cancer. The method may be repeated as necessary either to mitigate (i.e. prevent further growth) or to eliminate the cancer. Clinically, practice of the method will result in a reduction in the size or number of the cancerous growths and/or a reduction in associated symptoms (where applicable). Pathologically, practice of the method will produce at least one of the following: inhibition of cancer cell proliferation, reduction in the size of the cancer or tumor, prevention of further metastasis, and inhibition of tumor angiogenesis.

The compounds and compositions can be used in combination therapies. In other words, the compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved.

The synthesis of epothilone analogues as anticancer agents is based on the methodologies as follows:

Structural rigidification of the region between the macrolactone ring and the aromatic side-chain occurs by incorporating a single-carbon bridge between the C14 and C17 carbon atoms in the form of a substituted cyclopentene ring in order to generate molecules with proper orientation of structural residues for enhanced interaction with the tubulin receptor. Such molecules have improved pharmacologic profiles for development as potent anticancer agents. It is to be understood, that in other embodiments, the Ar can comprise phenyl, 2-prridyl or other heteroaromatic, and R can comprise a connecting link of variable hydrophobicity, length (usually 2 or 3 carbons) containing double bonds, or other heteroatom (such as N, O, S) functionality, and other combinations thereof.

Conformational Restrained Epothilone Analogues

Figure 2:
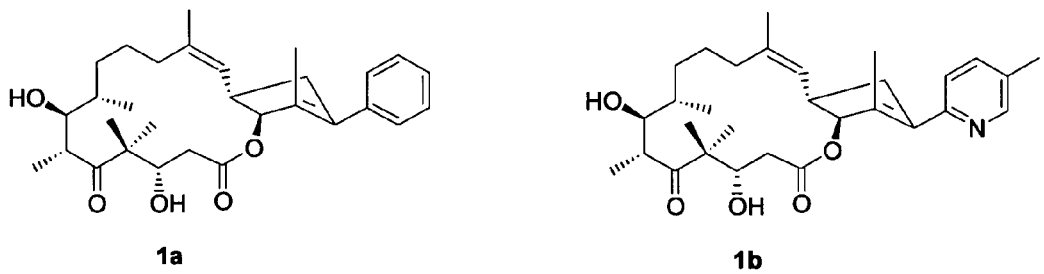
FIG. 2 shows conformationally restrained analogues of epothilones (compounds 1a and 1b) that are formed by restricting the mobility of the aromatic side chain.

In one particular aspect, there is provided herein a new class of conformationally restrained analogues of epothilones (compounds 1a and 1b, FIG. 2) that are formed by restricting the mobility of the aromatic side chain.

In the designed analogues, a single methylene bridge was introduced between C14 and C17. The resulting cyclopentene moiety, which incorporated the C16-C17 double bond, was designed to rigidify the side chain while still permitting sufficient mobility of the pyridine ring to allow for the preferred N-atom orientation for H-bonding interaction with the receptor.[17]

Figure 3:
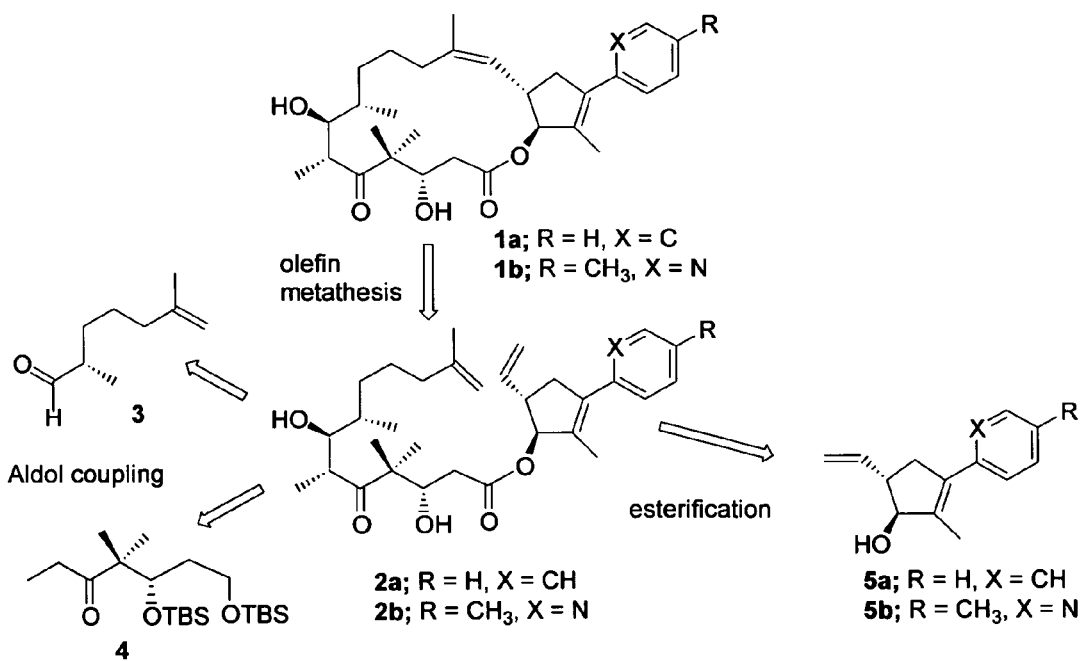
FIG. 3 shows retrosynthetic analysis of epothilones (Scheme 1).
Figure 12:
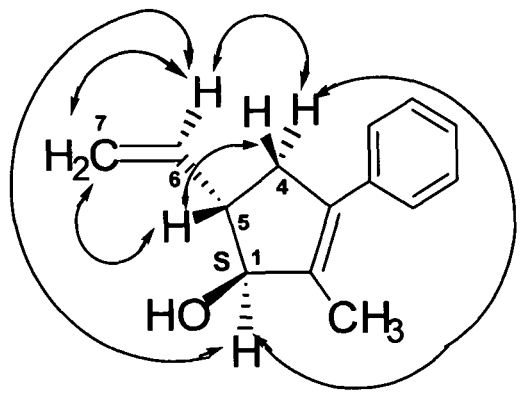

Synthesis and Selective Activity of Conformationally Restrained Epothilone Analogues A convergent synthetic approach with ring-closing metathesis (RCM) of 2a, and 2b in the final step was adapted, as shown in FIG. 3 showing Scheme 1.

Retrosynthetic disconnection of 2a and 2b led to the three key synthons 3, 4, and either 5a or 5b. The stereoselective aldol coupling product between aldehyde 3 and ketone 4 was converted to the corresponding carboxylic acid and then esterified with alcohols 5a and 5b to give 2a and 2b. This intermediate was subjected to RCM to yield the desired macrolide skeleton.

Aldehyde 3 was made using the Evans asymmetric alkylation protocol, as shown in Scheme 2 in FIG. 4.[28]

Wittig olefination of commercially available keto acid 6 gave the alkene 7. After converting to the acid chloride 8 with oxalyl chloride, coupling to the chiral auxiliary (S)-(−)-4-isopropyl-2-oxazolidinone gave the imide 9 in high yield. Imide 9 was then converted to the aldehyde 3 following Schinzer's procedure.[29]

The bis-(silyl ether) ketone 4 was made, as shown in Scheme 3 in FIG. 5. Aldehyde 10 was synthesized as reported earlier.[30] Selective reduction of the aldehyde group of 10 was accomplished using $NaBH_4$ in methylene chloride/ethanol solution to give the primary alcohol 11 as a mixture with its hemiacetal 12. The crude mixture was converted to the bis-silyl ether 4 with TBSCl and imidazole.

Highly diastereoselective aldol reaction between the aldehyde 3 and ketone 4 under kinetic control generated the aldol 13 (Scheme 4 in FIG. 6). The desired syn aldol 13 was formed together with the other syn diastereomer (10:1) without any detectable formation of the anti product.[15] The syn diastereomers were separated by column chromatography. The (S)-stereochemistry at C7 in 13 was confirmed by Mosher ester analysis.[31, 32] The hydroxyl function was protected with 2,2,2-trichloroethoxycarbonyl (Troc) group to give compound 14. The use of the Troc group in this context was based on an earlier failed sequence. We had initially approached the synthesis of 1a employing Suzuki coupling for making the C12-C13 double bond and Yamaguchi macrolactonization for final ring closure and using TBS (and later TES) protecting group at this position instead of Troc. However, desilylation of these groups in the final step posed an insurmountable problem. Milder desilylating agents were ineffective and harsher conditions resulted in the decomposition of the product. Thus, the present protocol was adopted using a Troc protecting group and olefin metathesis for final ring closure. Selective desilylation of the TBS group on the primary hydroxyl gave the alcohol 15, which was oxidized with Dess-Martin periodinane to the corresponding aldehyde 16. Pinnick's oxidation of aldehyde 16 gave the carboxylic acid 17.

The synthesis of enantiomerically pure β-ketoalcohols 22a and 22b via diastereoselective reduction of the corresponding β-ketoesters 21a and 21b was chosen as an approach to this moiety since the racemate of these β-ketoesters can be prepared by aldol cyclization of the corresponding γ-aryl-substituted β-ketoesters 20a and 20b, as shown in Scheme 5 in FIG. 7. We investigated the conversion of 21a and 21b to 22a and 22b in high enantiomeric purity.

The diketoesters 20a and 20b were synthesized by alkylation of ethyl propionylacetate 18 with substituted α-bromoacetoaromatic derivatives 19a and 19b (Scheme 5 in FIG. 7). They were cyclized directly into the cyclopentenones 21a and 21b by an intramolecular aldol condensation reaction. The synthesis of 2-bromoketone 19b was performed as shown in Scheme 6 in FIG. 8.[33] Bromination of 25 to 19b was carried out using polymer supported tribromide (Amberlyst A26-$Br_3^-$).[34]

After a number of unsuccessful attempts at stereoselective reduction of the ketone function of 21a, including reduction with high catalyst loading of Corey's oxazaborolidine CBS reagent,[35] catalytic hydrogenation using $BINAP \cdot RuCl_2$,[36] and Luche reduction with $NaBH_4$ and $CeCl_3$[37, 38] or $MgCl_2$, the desired trans product 22a and its enantiomer ent-22a were finally obtained in equal amounts by reduction under chelation control using $Zn(BH_4)_2$ (Scheme 7 in FIG. 9).[39, 40]

The trans racemate mixture 22a/ent-22a was efficiently separated by enzymatic resolution using Amano PS-D Lipase enzyme (Scheme 7 in FIG. 9). Alcohol 22a was acetylated to form 26, while ent-22a remained unchanged. They were separated by column chromatography (49% 26 and 48% ent-22a).

The stereochemistry at the secondary hydroxyl carbon of ent-22a isomer and its enantiomeric purity were determined by Mosher's ester analysis (R, 99% ee).[31, 32] Ethanolysis of 26 gave the desired alcohol 22a (S, 98% ee by Mosher's ester analysis).[31, 32] The trans configuration of 22a was confirmed by NOE experiment as described later.

Compound 21b was found to be much more resistant to reduction and could not be reduced with a variety of reducing agents, including $Zn(BH_4)_2$. Indeed, using even an excess of $NaBH_4$ resulted in only partial reduction. While not wishing to be bound by theory, the inventors herein believe that altering electronic effects exerted by the basic nitrogen atom could render the molecule susceptible to reduction.

The inventors herein then discovered that prior conversion of 21b to the corresponding trifluoroacetate salt by treatment with two equivalents of trifluoroacetic acid (TFA) and removal of excess TFA, under vacuum rendered the molecule more susceptible to $NaBH_4$ reduction, which occurred rapidly to produce a mixture of all four diastereomers, as shown in Scheme 8 in FIG. 10). The product mixture was separated into two enantiomeric pairs of cis and trans diastereomers by column chromatography (trans:cis 2:1 by $^1H$ NMR). The larger fraction containing the pair of trans enantiomers (22b, ent-22b) was resolved using Amano PS-D Lipase enzyme as described earlier for the phenyl analogue.

As with the phenyl analogue, the desired enantiomer 22b was acetylated to 28 while the enantiomer ent-22b remained unchanged. They were separated by column chromatography and 28 was subjected to ethanolysis as before to obtain 22b (S, 95% ee by Mosher's ester analysis).[31, 32] NOE experiments confirmed the trans configuration of the molecule. The cis isomers 27 and ent-27, isolated by a similar enzyme-mediated resolution protocol, showed a strong NOE between the two protons at the two stereogenic centers, and no such NOE was observed between the two corresponding protons in 22b or ent-22b.

Reduction of the ester group of silyl ethers 29a and 29b with DIBAL-H gave the corresponding aldehydes 30a and 30b, which were subjected to Wittig olefination to obtain the olefins 31a and 31b, as shown in Scheme 9 in FIG. 11.

Desilylation of 31a and 31b with TBAF gave the desired alcohols 5a and 5b. At this stage, we confirmed the relative trans stereochemistry of the protons H1 and H5 in the cyclopentene moiety 5a and the absolute stereochemistry of the molecule as shown based on NOE correlations (see FIG. 3) in conjunction with the already established S-configuration of the secondary hydroxyl carbon.[31, 32]

Figure 13:
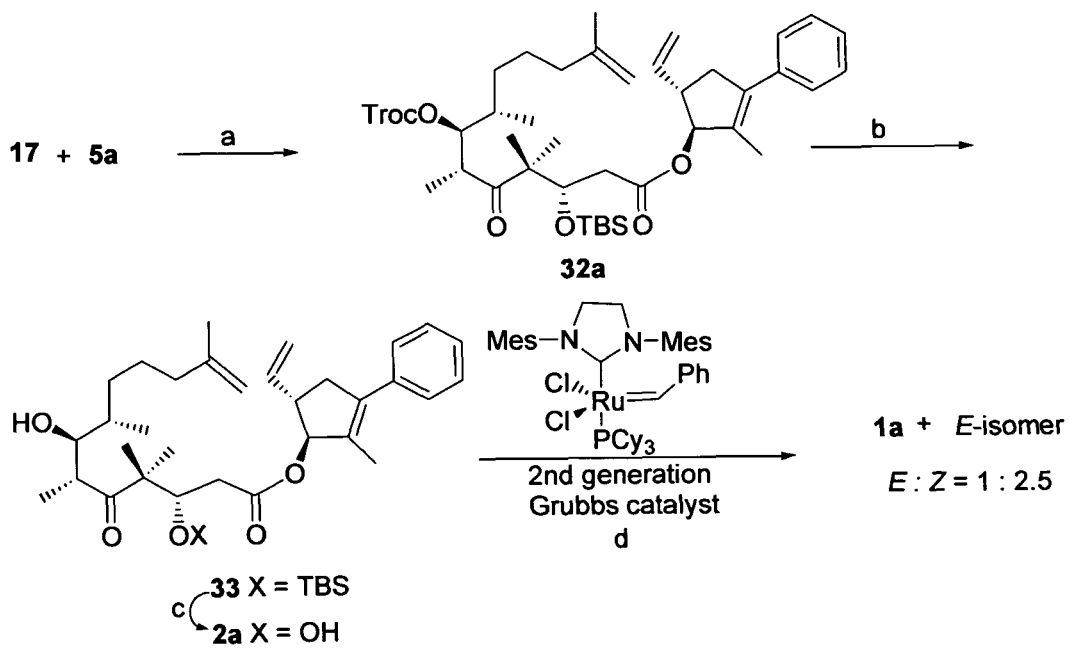
FIG. 13 shows synthesis of intermediate 1a (Scheme 10).

The carboxylic acid 17 was esterified to 32a with alcohol 5a using DCC/DMAP, as shown in Scheme 10 in FIG. 13.

The Troc and TBS protecting groups were sequentially removed with zinc dust/ammonium chloride in dry ethanol and TAS-F,[41] respectively, to give intermediate 2a. Finally, RCM of 2a using second generation Grubbs' catalyst gave the desired Z-alkene 1a, accompanied by what appeared to be the E-isomer as a minor product. A strong NOE correlation between the C12-methyl protons and the C13 olefinic proton confirmed the Z-stereochemistry of the double bond of 1a.

Figure 14:
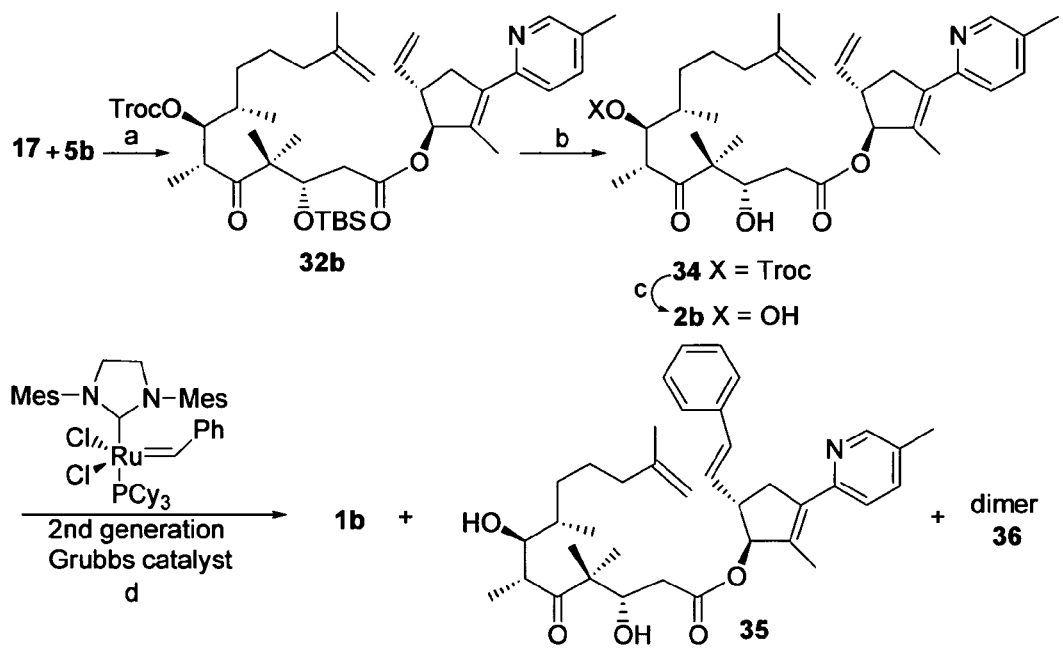
FIG. 14 shows synthesis of intermediate 1b (Scheme 11).

A similar approach to synthesize the pyridine analogue 1b starting from the carboxylic acid 17 and the alcohol 5b was complicated by an unexpected retro-aldol decoupling of the alcohol obtained by the removal of Troc protecting group upon treatment with TAS-F. This was overcome by changing the order of removal of the two protecting groups, as shown in Scheme 11 in FIG. 14.

Thus, the TBS protecting group was removed first with TAS-F[41] to give 34 which was then treated directly with zinc dust and ammonium chloride in dry ethanol to give intermediate 2b. Finally, RCM of 2b using second generation Grubbs' catalyst gave the desired product 1b. The Z-configuration of the double bond was confirmed by NOESY. Two by-products, the phenyl analogue 35 and a dimer were also isolated. A large coupling constant between the two olefinic protons and the absence of NOE correlations established the E-configuration of the non-terminal double bond of 35. Formation of 35 can be attributed to high catalyst loading required to overcome the sluggishness of the RCM reaction.

Strong Growth Inhibitory Activity on CCRF-CEM and SR Leukemia Cell Lines

Figure 21:
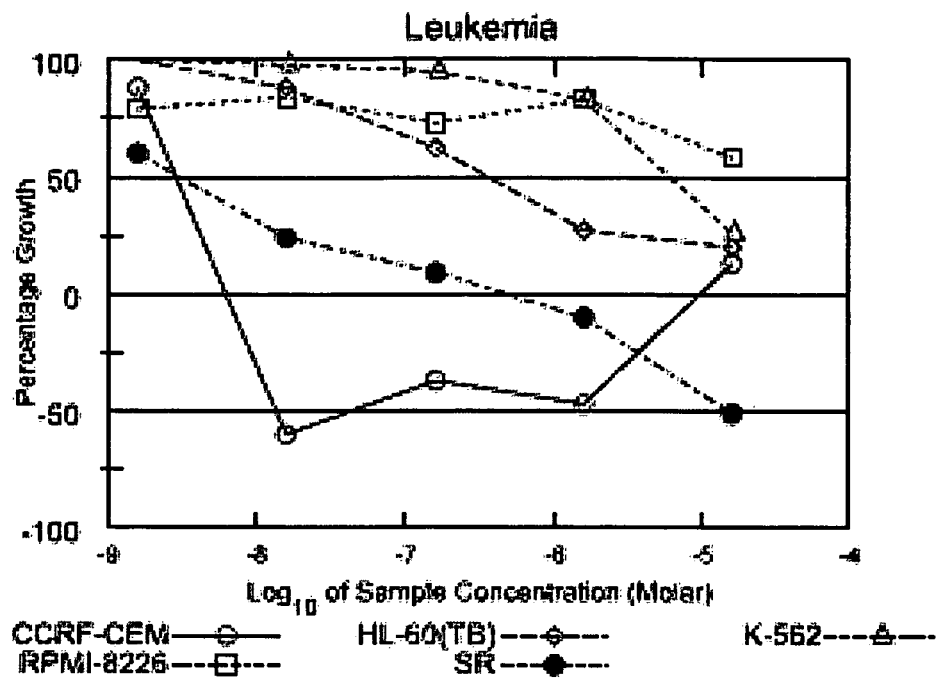
FIG. 21 is a graph showing in vitro 60 cell line human tumor screen Dose Response Curves for Leukemia.
Figure 22:
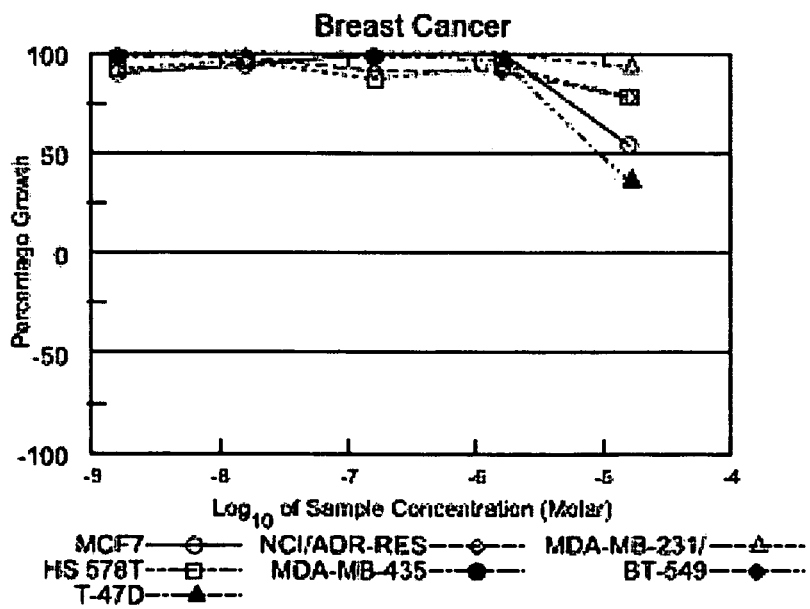
FIG. 22 is a graph showing in vitro 60 cell line human tumor screen Dose Response Curves for Breast Cancer.
Figure 23:
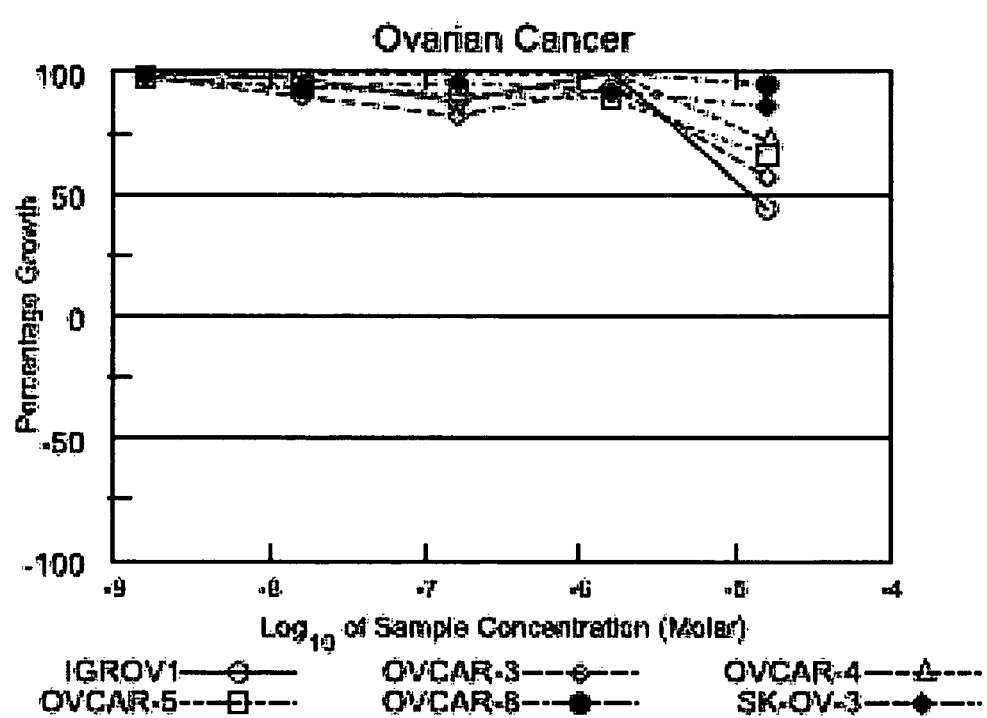
FIG. 23 is a graph showing in vitro 60 cell line human tumor screen Dose Response Curves for Ovarian Cancer.

Compound 1b showed strong growth inhibitory activity on CCRF-CEM and SR leukemia cell lines with $GI_{50}$ values of 2.7 and 2.9 nM, respectively, in the NCI in vitro 60 cell line human tumor screen, but showed no significant activity on any of the others, including breast cancer and ovarian cancer cell lines, as shown in the data in FIGS. 21, 22 and 23. While it is currently not possible to make a direct comparison of the performance of this compound vis-a-vis natural epothilones as data on the activity of natural epothilones in the NCI 60 cell line assay are not available, it is significant to note that the mechanistically analogous cancer drug paclitaxel (taxol) is less selective and is also less effective against these two cell lines ($GI_{50}$ of 12.6 nM for CCRF-CEM and 15.8 nM for SR).

The inventors then subjected the open-chain analogue 35, which was isolated as a by-product of the RCM reaction along with 1b, as well to the NCI 60 cell line assay, but it showed no significant activity on any of the cell lines. Also, the inventors have subjected analogue 1a to a preliminary growth inhibition assay on BCF-7 breast cancer cells, in which it showed no activity.

Thus, a particular aspect of the present invention is the successful synthesis of two novel conformationally restrained epothilones 1a and 1b.

Figure 15:
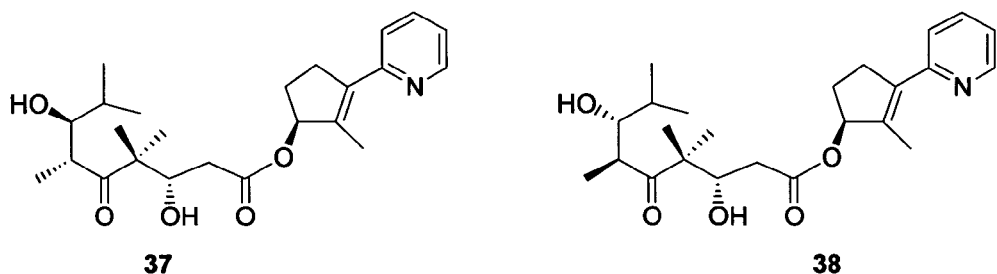
FIG. 15 shows open-chain epothilones 37 and 38.

Another particular aspect of the present invention is the strategy described herein that is applicable to the synthesis of other important analogues of the series. For example, the inventors herein have also prepared two acyclic diastereomeric analogues 37 and 38, as shown in FIG. 15.[42] Compound 37 with the acyl fragment stereochemistry as found in the natural product had weak activity against two cancer cell lines. Though the activity was low, it is believed that the acyl fragment and its link through the present inventive rigidifying element to the pyridyl side chain still allowed expression of activity.

In another particular aspect, while there is considerable distance between the high activity of 1b and low activity of 37, it is now believed that the present inventive methods allows for the preparation of additional compounds somewhere between—simpler than 1b, but more complex than 37, possessing just the necessary and sufficient rigidity to promote a high level of selective activity.

The strong and selective growth inhibitory effect exhibited by analogue 1b on two leukemia cell lines, while not suppressing the proliferation of breast cancer and ovarian cancer cells which are very sensitive to natural epothilones, indicates that it is now possible also to develop new lead molecules of varying pharmacological profile by substantial modification of the epothilone scaffold.

The present inventive method also allows for the preparation of new classes of conformationally-restrained epothilone analogues to increase selectivity and potency.

EXAMPLES

The examples below are used for a more detailed explanation, without intending that it be limited to these examples.

Materials and Methods

General Techniques. All reactions were carried out under an argon or nitrogen atmosphere using dry solvents under anhydrous conditions, unless otherwise noted. Tetrahydrofuran (THF) and diethyl ether were distilled under nitrogen from sodium-benzophenone. The solvents used were ACS grade from Fisher. Yields refer to chromatographically and spectroscopically ($^1H$ NMR) homogeneous materials, unless otherwise noted. Reagents were purchased from Aldrich and Acros, and used without further purification. Reactions were monitored by thin-layer chromatography (TLC) carried out on 0.20 mm POLYGRAM® SIL silica gel plates (Art.-Nr. 805 023) with fluorescent indicator $UV_{254}$ using UV light and 15% sulfuric acid in ethanol solution and heat as visualizing agents. Normal phase flash column chromatography was carried out using Davisil® silica gel (100-200 mesh, Fisher). Preparative thin-layer chromatography (PTLC) separations were carried out on 1 mm, or 2 mm E. Merck silica gel plates (60F-254). NMR spectra were recorded on INOVA 600, Varian VXRS-400, Bruker AC-F 300 MHz, or Nicolet NM-500 MHz (modified with a Tecmag Libra interface) instruments and calibrated using residual undeuterated solvent as an internal reference. Coupling constants (J) were expressed in Hertz. Attached proton tests (APT) were performed to distinguish between different carbons in the $^{13}C$ NMR spectra. The following abbreviations were used to explain the multiplicities: s=singlet, d=doublet, t=triplet, q=quartet, m=multiplet, and b=broad. Optical rotations were recorded on an AUTOPOL® III 589/546 polarimeter. High-resolution mass spectra (HRMS) were recorded on a Micromass LCT Electrospray mass spectrometer performed at the Mass Spectrometry & Proteomics Facility (The Ohio State University). (+)-Allyldiisopinocamphenylborane solution in pentane was prepared by an adaptation of a procedure reported by Brown et al.[1] Allylmagnesium bromide (5.82 ml of 1 M solution in ether, 5.82 mmol) was added dropwise to a well-stirred solution of (−)-B-methoxydiisopinocamphenylborane (1.92 g, 6.062 mmol) in ether (35 ml) at 0° C. After addition was complete, the reaction mixture was stirred at room temperature for 1 h, and the solvents were pumped off under reduced pressure. The residue was extracted with dry pentane (3×13 ml) under nitrogen, and the stirring was discontinued to allow the precipitation of the MgBr(OMe) salt. The clear pentane supernatant was cannulated into another flask through a filtering funnel, and used without further purification.

Zinc borohydride (0.3M solution in dry ether) was prepared by addition of saturated solution of anhydrous zinc chloride (12 g, 88.05 mmol, oven dried at 130° C. for 8 h under vacuum) in ether (50 ml) to $NaBH_4$ (8.1 g) in ether (150 ml).[2, 3]

General procedure for Mosher Ester: To a stirred solution of alcohol (1 equiv), DMAP (0.5 equiv), and triethylamine (3 equiv) in methylene chloride was added (S)-(+)- or (R)-(−)-α-methoxy-α-(trifluoromethyl)phenylacetyl chloride (MTPACl) (3 equiv) at room temperature. The resulting mixture was stirred overnight. The solution was diluted with ethyl acetate and washed with water, dried, and concentrated in vacuo. Purification by silica gel column chromatography will furnish the Mosher Ester.

6-Methyl-hept-6-enoic acid (7)

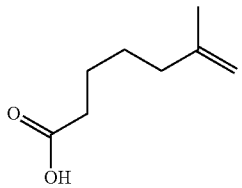

n-Butyllithium (10.8 ml of 2.5 M in hexanes, 27 mmol, 1.3 equiv) was added to a solution of methyltriphenylphosphonium bromide (9.7 g, 27 mmol, 1.3 equiv) in dimethyl sulfoxide (50 ml) at 0° C., and the mixture was stirred at room temperature for 1 h. It was added to a solution of 6-oxoheptanoic acid 6 (3 g, 20.82 mmol, 1 equiv) and n-butyllithium (8.33 ml of 2.5 M in hexanes, 20.82 mmol, 1 equiv) in THF (30 ml). The mixture was stirred at room temperature for 48 hr. Water was added and the mixture was acidified with 2 N HCl and extracted with methylene chloride (3×50 ml). The organic layer was washed with 10% sodium hydroxide solution. The aqueous layer was acidified with 2 N HCl and extracted with ethyl acetate (3×60 ml). The organic extracts were dried over anhydrous sodium sulfate and concentrated in vacuo. Purification by flash column chromatography (10% EtOAc/hexanes) gave pure acid 7 (2.32 g, 78%) as a colorless oil: TLC $R_f$=0.47 (silica gel, 25% EtOAc/hexanes); $^1$H NMR (600 MHz, CDCl$_3$) δ 4.69 (s, 1H), 4.65 (s, 1H), 2.34 (t, J=7.8 Hz, 2H), 2.01 (t, J=7.8 Hz, 2H), 1.69 (s, 3H), 1.64-1.58 (m, 2H), 1.50-1.44 (m, 2H); $^{13}$C NMR (100 MHz, CDCl$_3$) δ 180.7, 145.6, 110.4; 37.5, 34.2, 27.1, 24.4, 22.5.

6-Methyl-hept-6-enoyl chloride (8)

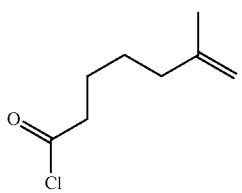

To a solution of the carboxylic acid 7 (2.2 g, 15.5 mmol) in benzene (30 ml), was added oxalyl chloride (3 ml, 34.4 mmol, 2.22 equiv). A drying tube was placed on the flask and the reaction mixture was stirred for 90 min at room temperature before it was concentrated in vacuo. The crude acid chloride 8 was used in the next step without further purification: TLC $R_f$=0.37 (silica gel, 25% EtOAc/hexanes); $^1$H NMR (600 MHz, CDCl$_3$) δ 4.69 (s, 1H), 4.67 (s, 1H), 2.88 (t, J=7.8 Hz, 2H), 2.02 (t, J=7.8 Hz, 2H), 1.74-1.66 (m, 2H), 1.69 (s, 3H), 1.58-1.46 (m, 2H); $^{13}$C NMR (100 MHz, CDCl$_3$) δ 173.9, 145.1, 110.7, 46.7, 37.3, 26.4, 24.8, 22.4.

(4S)-4-Isopropyl-3-(6-methyl-hept-6-enoyl)-oxazolidin-2-one (9)

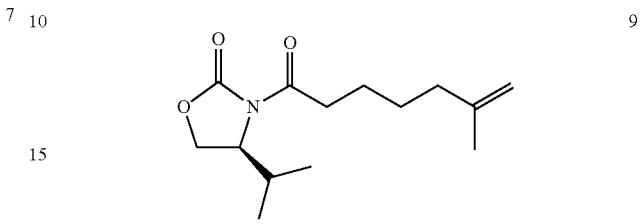

To a solution of (5)-4-isopropyl-2-oxazolidonone (1.56 g, 12.1 mmol, 1 equiv) in THF (40 ml) at −78° C. was added n-butyllithium (4.84 ml of a 2.5 M solution in hexanes, 12.1 mmol, 1 equiv). After 15 min acid chloride 8 (2.14 g, 13.3 mmol, 1.1 equiv) was added and the mixture was stirred for 30 min at −78° C. and for 15 min at 0° C. Saturated aqueous ammonium chloride (10 ml) was added and the resulting slurry was concentrated in vacuo. The residue was diluted with ether and washed successively with saturated aqueous sodium bicarbonate and brine. The organic layer was dried over anhydrous sodium sulfate, filtered, and concentrated in vacuo. Purification by flash chromatography (10% EtOAc/hexanes) gave imide, 9 (2.94 g, 96%) as a colorless oil: $[\alpha]^{22}_D$=+66.7 (c=0.6, CHCl$_3$); TLC $R_f$=0.40 (silica gel, 25% EtOAc/hexanes); $^1$H NMR (600 MHz, CDCl$_3$) δ 4.68 (s, 1H), 4.66 (s, 1H), 4.43-4.40 (m, 1H), 4.25 (t, J=9.0 Hz, 1H), 4.19 (dd, J=3.0 Hz, 9.0 Hz, 1H), 3.01-2.83 (m, 2H), 2.38-2.32 (m, 1H), 2.02 (t, J=7.8 Hz, 2H), 1.69 (s, 3H), 1.67-1.61 (m, 2H), 1.51-1.46 (m, 2H), 0.90 (d, J=7.2 Hz, 3H), 0.85 (d, J=7.2 Hz, 3H); $^{13}$C NMR (100 MHz, CDCl$_3$) δ 173.5, 154.3, 145.8, 110.2, 63.6, 58.6, 37.7, 35.6, 28.6, 27.2, 24.3, 22.6, 18.2, 14.9; HRMS calcd for C$_{14}$H$_{23}$NO$_3$+Na$^+$ 276.1576; found 276.1567 [M+Na$^+$].

(2S)-2,6-Dimethyl-hept-6-enal (3)

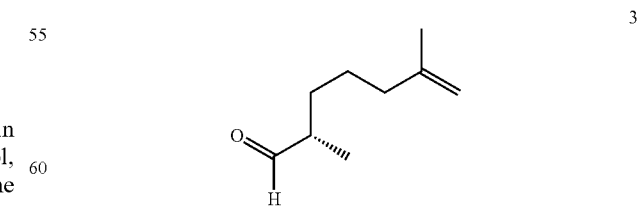

As reported by Schinzer et al.[4]: $[\alpha]^{22}_D$=+11.8 (c=0.5, CHCl$_3$); TLC $R_f$=0.64 (silica gel, 25% EtOAc/hexanes); $^1$H NMR (600 MHz, CDCl$_3$) δ 9.56 (d, J=1.8 Hz, 1H), 4.66 (s, 1H), 4.62 (s, 1H), 2.34-2.28 (m, 1H), 1.98 (t, J=7.8 Hz, 2H), 1.69-1.62 (m, 4H), 1.48-1.27 (m, 3H), 1.05 (d, J=6.6 Hz, 3H); $^{13}$C NMR (100 MHz, CDCl$_3$) δ 205.3, 145.4, 110.4, 46.4, 37.8, 30.2, 24.9, 22.4, 13.5.

(5S)-5,7-Bis-(tert-butyl-dimethyl-silanyloxy)-4,4-dimethyl-heptan-3-one (4)

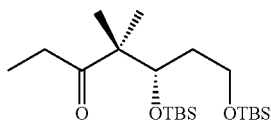

4

Sodium borohydride (570 mg, 15.4 mmol, 2 equiv) was dissolved in methylene chloride (175 ml) and dry ethanol (75 ml). The mixture was cooled to −78° C. for 15 min after which a solution of aldehyde 10[5] (2.2 g, 7.7 mmol, 1 equiv) in methylene chloride (5 ml) was added. After stirring for 1 h water (6 ml) was added and the reaction mixture was allowed to warm to room temperature. Methylene chloride (400 ml) was added and the mixture was washed with saturated aqueous sodium bicarbonate before it was dried over anhydrous sodium sulfate and concentrated in vacuo to give crude alcohol mixture 11 and 12. The crude alcohol mixture was dissolved in methylene chloride (40 ml) and cooled to 0° C. Imidazole (3.14 g, 46.15 mmol, 6 equiv) and tert-butyldimethylsilyl chloride (3.47 g, 23.1 mmol, 3 equiv) were added and the reaction mixture was stirred at room temperature for 16 hr. Saturated aqueous ammonium chloride (30 ml) was added and the layers were separated. The aqueous layer was further extracted with ethyl acetate (3×30) and combined organic extracts were dried over anhydrous sodium sulfate and concentrated in vacuo. Purification by flash chromatography (1%-5% EtOAc/Hexanes) gave the bis(silylether) 4 (2.5 g, 81% over two steps) as a colorless oil: $[α]^{22}{}_D$=−7.4 (c=1.8, CHCl$_3$); TLC R$_f$=0.70 (silica gel, 20% EtOAc/hexanes); $^1$H NMR (600 MHz, CDCl$_3$) δ 4.06 (dd, J=7.6 Hz, 3.0 Hz, 1H), 3.62-3.54 (m, 2H), 2.57-2.41 (m, 2H), 1.56-1.42 (m, 2H), 1.09 (s, 3H), 1.02 (s, 3H), 0.99 (t, J=7.0 Hz, 3H), 0.86 (s, 9H), 0.85 (s, 9H), 0.07 (s, 3H), 0.02 (s, 3H), 0.01 (s, 3H), 0.002 (s, 3H); $^{13}$C NMR (100 MHz, CDCl$_3$) δ 215.8, 73.6, 60.3, 53.2, 37.5, 31.8, 26.3, 26.1, 22.4, 20.2, 18.5, 18.4, 7.9, −3.8, −5.1; HRMS calcd for C$_{21}$H$_{46}$O$_3$Si$_2$+Na$^+$ 425.2883; found 425.2885 [M+Na$^+$].

(3S,6R,7S,8S)-1,3-Bis-(tert-butyl-dimethyl-silanyloxy)-7-hydroxy-4,4,6,8,12-pentamethyl-tridec-12-en-5-one (13)

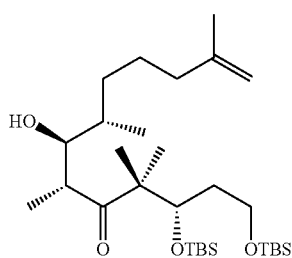

13

A solution of ketone 4 (1.8 g, 4.48 mmol, 2.3 equiv) in THF (5 ml) was added dropwise to a solution of freshly prepared LDA in THF [prepared by adding n-butyllithium (2.92 ml of 1.6 M solution in hexanes, 4.67 mmol) to diisopropylamine (4.67 mmol, 0.655 ml) in THF (5 ml) at −78° C., then warming the solution to 0° C. for 20 min, and finally cooling back to −78° C.]. The reaction mixture was stirred at −78° C. for 1 h and at −40° C. for 30 min and was cooled back to −78° C. A pre-cooled (−78° C.) solution of aldehyde 3 (0.272 g, 1.95 mmol, 1 equiv) in THF (10 ml) was then added via cannula to the mixture over 2 min. The reaction mixture was stirred at −78° C. for 15 min before it was quenched rapidly by injection of a solution of acetic acid (0.55 ml) in THF (1.64 ml). The mixture was stirred at −78° C. for 5 min and brought to room temperature. Saturated aqueous ammonium chloride (20 ml) and ether (25 ml) were added and the layers were separated. The aqueous layer was extracted with ether (3×25 ml) and the organic extracts were combined, dried over anhydrous sodium sulfate, and concentrated in vacuo. Flash column chromatography (4-20% ether/hexanes) gave recovered ketone 4 (0.78 g) followed by syn aldol 13 (0.87 g, 83%) as the pure diastereomer along with other syn aldol diastereomer (74 mg, 7%) as colorless oils: $[α]^{22}{}_D$=−39.6 (c=0.7, CHCl$_3$); TLC R$_f$=0.57 (silica gel, 20% ether/hexanes); $^1$H NMR (600 MHz, CDCl$_3$) δ 4.66 (s, 1H), 4.65 (s, 1H), 3.88 (dd, J=2.4 Hz, 7.8 Hz, 1H), 3.67-3.63 (m, 1H), 3.60-3.55 (m, 1H), 3.30-3.27 (m, 2H), 2.05-1.95 (m, 2H), 1.69 (s, 3H), 1.76-1.26 (m, 7H), 1.19 (s, 3H), 1.07 (s, 3H), 1.01 (d, $^3$J=6.6 Hz, 3H), 0.88 (s, 9H), 0.87 (s, 9H), 0.82 (d, J=7.2 Hz, 3H), 0.09 (s, 3H), 0.06 (s, 3H), 0.02 (s, 6H); $^{13}$C NMR (100 MHz, CDCl$_3$) δ 222.7, 146.5, 109.9, 75.1, 74.3, 60.7, 54.2, 41.5, 38.4, 35.7, 32.8, 26.4, 26.3, 26.2, 25.0, 23.1, 22.6, 20.7, 18.6, 18.5, 15.6, 9.8, −3.5, −3.8, −5.0; HRMS calcd for C$_{30}$H$_{62}$O$_4$Si$_2$+Na$^+$ 565.4084; found 565.4067 [M+Na$^+$].

(3S,6R,7S,8S)-Carbonic acid-1-[4,6-bis-(tert-butyl-dimethyl-silanyloxy)-1,3,3-trimethyl-2-oxo-hexyl]-2,6-dimethyl-1-hept-6-enyl ester 2,2,2-trichloro-ethyl ester (14)

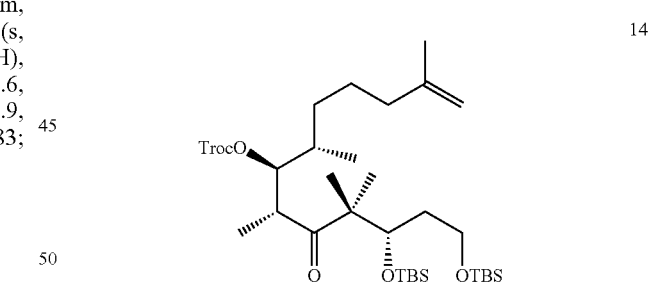

14

To a solution of aldol 13 (0.80 g, 1.48 mmol) in methylene chloride (30 ml) at 0° C. was added pyridine (0.96 ml, 11.84 mmol, 8 equiv) followed by 2,2,2-trichloroethyl chloroformate (0.8 ml, 5.92 mmol, 4 equiv), and the reaction mixture was stirred at 0° C. for 1 h. Saturated aqueous sodium bicarbonate (50 ml) was added and the organic layer was separated. The aqueous layer was extracted with methylene chloride (3×50 ml), and the combined organic layers were dried over anhydrous sodium sulfate and concentrated in vacuo. Purification by flash column chromatography (2% EtOAc/hexanes) afforded protected aldol 14 (0.98 g, 93%) as a colorless oil: $[α]^{22}{}_D$=−51.5 (c=1.6, CHCl$_3$); TLC R$_f$=0.72 (silica gel, 17% EtOAc/hexanes); $^1$H NMR (600 MHz, CDCl$_3$) δ 4.85 (d, J=12.0 Hz, 1H), 4.78 (dd, J=4.2 Hz, 7.8 Hz, 1H), 4.66 (d, J=12.0 Hz, 1H), 4.66 (s, 1H), 4.62 (s, 1H), 3.72 (dd, J=2.4

Hz, 7.8 Hz, 1H), 3.63-3.59 (m, 1H), 3.58-3.53 (m, 1H), 3.50-3.45 (m, 1H), 1.98-1.91 (m, 2H), 1.72-1.61 (m, 2H), 1.67 (s, 3H), 1.51-1.42 (m, 2H), 1.34 (s, 3H), 1.31-1.24 (m, 3H), 1.04 (d, J=6.6 Hz, 3H), 0.99 (s, 3H), 0.94 (d, J=6.6 Hz, 3H), 0.88 (s, 9H), 0.85 (s, 9H), 0.082 (s, 6H), 0.001 (s, 6H); $^{13}$C NMR (100 MHz, CDCl$_3$) δ 215.8, 154.5, 145.8, 110.3, 95.0, 83.1, 76.8, 75.8, 60.5, 53.8, 42.7, 38.2, 34.9, 31.5, 26.4, 26.1, 24.9, 23.7, 22.6, 21.2, 18.6, 16.3, 11.3, −3.3, −4.1, −5.0, −5.1; HRMS calcd for $C_{33}H_{63}Cl_3O_6Si_2+Na^+$ 739.3126; found 739.3163 [M+Na$^+$].

(3S,6R,7S,8S)-Carbonic acid-1-[4-(tert-butyl-dimethyl-silanyloxy)-6-hydroxy-1,3,3-trimethyl-2-oxo-hexyl]-2,6-dimethyl-1-hept-6-enyl ester 2,2,2-trichloro-ethyl ester (15)

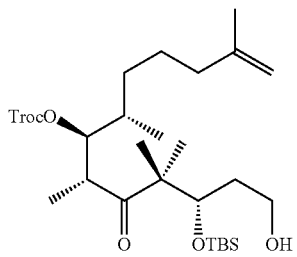

A solution of bis-silyl compound 14 (0.8 g, 1.11 mmol, 1 equiv) in methylene chloride (30 ml) and methanol (20 ml) was cooled to 0° C. To this solution was added a solution of (1S)-(+)-10-camphorsulfonic acid (77 mg, 0.33 mmol, 0.3 equiv) in methanol (10 ml). The reaction mixture was stirred at 0° C. for 7 h before it was quenched with saturated aqueous sodium bicarbonate (10 ml). The solid precipitate was filtered and the filtrate was concentrated in vacuo. The residue was diluted with ether (100 ml) and washed with brine. The organic layer was separated and the aqueous layer was extracted with ether (3×20 ml). The combined organic phases were dried over anhydrous sodium sulfate and concentrated in vacuo. Purification by flash column chromatography (10% EtOAc/hexanes) afforded the unstable alcohol 15 (0.583 g, 87%). It was used directly in the next step; TLC $R_f$=0.57 (silica gel, 33% EtOAc/hexanes); $^1$H NMR (600 MHz, CDCl$_3$) δ 4.87-4.80 (m, 2H), 4.69-4.61 (m, 3H), 3.92 (dd, J=3.0 Hz, 7.8 Hz, 1H), 3.67-3.59 (m, 2H), 3.45-3.40 (m, 1H), 1.98-1.90 (m, 2H), 1.66 (s, 3H), 1.70-1.42 (m, 8H), 1.26 (s, 3H), 1.07-1.06 (m, 6H), 0.95 (d, J=6.6 Hz, 3H), 0.89 (s, 9H), 0.10 (s, 3H), 0.08 (s, 3H); HRMS calcd for $C_{27}H_{49}Cl_3O_6Si+Na^+$ 625.2262; found 625.2260 [M+Na$^+$].

(3S,6R,7S,8S)-3-(tert-butyl-dimethyl-silanyloxy)-4,4,6,8,12-pentamethyl-5-oxo-7-(2,2,2-trichloro-ethoxycarbonyloxy)-tridec-12-enoic acid (17)

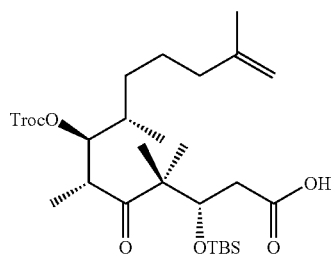

Dess-Martin periodinane (0.545 g, 1.28 mmol, 1.4 equiv) was added to a solution of alcohol 15 (0.550 g, 0.914 mmol) in methylene chloride (4 ml). The mixture was stirred at room temperature for 15 min. Additional amount of Dess-Martin reagent (0.23 g, 0.6 equiv) was added and the reaction mixture was stirred for 15 min and then was subjected to flash column chromatography (10% EtOAc/hexanes) to furnish crude aldehyde 16 that was used directly in the next step. A solution of sodium dihydrogenphosphate (270 mg, 2.25 mmol, 2.46 equiv) and sodium chlorite (270 mg, 3 mmol, 3.27 equiv) in distilled water (5 ml) was added to the crude aldehyde 16 (ca 0.914 mmol) in t-butanol (25 ml) and 2-methyl-2butene (6 ml). The mixture was stirred at room temperature for 1 h and quenched by addition of saturated aqueous ammonium chloride (50 ml) and water (50 ml). The mixture was extracted with ethyl acetate (3×60 ml), and the combined organic extracts were dried over anhydrous sodium sulfate and concentrated in vacuo. Purification by flash column chromatography (10% EtOAc/hexanes) afforded the pure carboxylic acid 17 (0.505 g, 90% over two steps) as a colorless oil; [α]$^{22}_D$=−53.7 (c=0.8, CHCl$_3$); TLC $R_f$=0.58 (silica gel, 40% EtOAc/hexanes); $^1$H NMR (600 MHz, CDCl$_3$) δ 4.85 (d, J=12.0 Hz, 1H), 4.76 (dd, J=4.2 Hz, 7.2 Hz, 1H), 4.66 (d, J=12.0 Hz, 1H), 4.66 (s, 1H), 4.62 (s, 1H), 4.22 (dd, J=3.6 Hz, 6.6 Hz, 1H), 3.47-3.41 (m, 1H), 2.60 (dd, J=3.6 Hz, 17.4 Hz, 1H), 2.21 (dd, J=6.6 Hz, 16.8 Hz, 1H), 1.96-1.91 (m, 2H), 1.74-1.68 (m, 1H), 1.66 (s, 3H), 1.52-1.42 (m, 2H), 1.31 (s, 3H), 1.28 (d, J=16.8 Hz, 3H), 1.06 (s, 6H), 0.94 (d, J=7.2 Hz, 3H), 0.86 (s, 9H), 0.1 (s, 3H), 0.03 (s, 3H); $^{13}$C NMR (100 MHz, CDCl$_3$) δ 215.5, 177.7, 154.5, 145.8, 110.3, 94.9, 82.7, 76.9, 75.0, 53.8, 42.4, 39.9, 38.2, 34.9, 31.5, 26.3, 26.2, 24.8, 23.0, 22.6, 20.3, 18.4, 16.3, 11.5, −4.3; HRMS calcd for $C_{27}H_{47}Cl_3O_7Si+Na^+$ 639.2054; found 639.2079 [M+Na$^+$].

3-Oxo-2-(2-oxo-2-phenyl-ethyl)-pentanoic acid ethyl ester (20a)

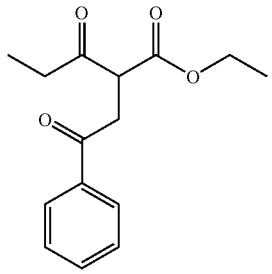

Ethyl propionylacetate 18 (10 g, 69.4 mmol) was added slowly to a stirred suspension of sodium hydride (60% dispersion in mineral oil, 3.33 g, 83.3 mmol, 1.2 equiv) in THF (100 ml) at 0° C. and the mixture was stirred for 30 min. 2-Bromoacetophenone 19a (15.2 g, 76.34 mmol, 1.1 equiv) in THF (10 ml) was added dropwise and the reaction mixture was stirred at room temperature for 16 h. Saturated aqueous ammonium chloride (60 ml) was added and the mixture was subsequently extracted with diethyl ether (3×70 ml). The combined organic layers were washed with brine and dried over anhydrous sodium sulfate. The solvent was removed in vacuo to give a dark yellow oil that was purified by flash column chromatography (10% EtOAc/hexane) to give the diketoester 20a (14.8 g, 82%) as a yellow oil: TLC $R_f$=0.50 (silica gel, 25% EtOAc/hexanes); $^1$H NMR (400 MHz, CDCl$_3$) δ 7.98 (d, J=8.4 Hz, 2H), 7.58 (m, 1H), 7.46 (m, 2H), 4.22 (q, J=7.2 Hz, 3H), 3.74 (dd; J=8.4 Hz, 18.4 Hz, 1H), 3.53 (dd, J=5.2 Hz, 18.4 Hz, 1H), 2.91-2.70 (m, 2H), 1.28 (t, J=7.2 Hz, 3H), 1.12 (t, J=7.2 Hz, 3H); $^{13}$C NMR (75 MHz, CDCl$_3$) δ 205.4, 197.4, 169.3, 136.3, 133.6, 128.8, 128.3, 61.9, 53.2, 37.7, 36.6, 14.2, 7.8; HRMS calcd for C$_{15}$H$_{18}$O$_4$+Na$^+$ 285.1103; found 285.1093 [M+Na$^+$].

3-Methyl-2-oxo-4-phenyl-cyclopent-3-enecarboxylic acid ethyl ester (21a)

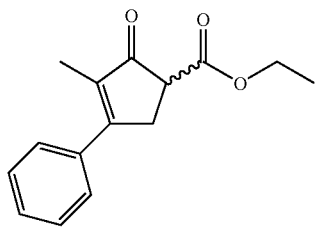

21a

A solution of the diketoester 20a (12 g, 45.8 mmol) in dry ethanol (150 ml) was added dropwise to a solution of sodium hydroxide (1.83 g, 45.8 mmol) in dry ethanol (75 ml) with vigorous stirring. The solution was heated to 50° C. and stirred overnight at that temperature. Ether (1.5 L) was added and the organic phase was washed with 2 N HCl (3×300 ml) and dried over anhydrous sodium sulfate. The solvent was removed in vacuo to give an oil that was purified by flash column chromatography (6% EtOAc/hexane) to give the cyclic β-ketoester 21a (8.7 g, 78%) as a yellow oil: TLC R$_f$=0.40 (silica gel, 25% EtOAc/hexane); $^1$H NMR (400 MHz, CDCl$_3$) δ 7.56-7.52 (m, 2H), 7.50-7.42 (m, 3H), 4.26 (q, J=7.2 Hz, 2H), 3.58 (dd, J=3.2 Hz, 7.6 Hz, 1H), 3.38-3.31 (m, 1H), 3.15-3.07 (m, 1H), 1.99 (s, 3H), 1.32 (t, J=7.2 Hz, 3H); $^{13}$C NMR (75 MHz, CDCl$_3$) δ 202.6, 169.6, 166.5, 135.8, 134.9, 130.2, 128.9, 127.9, 61.9, 51.3, 33.7, 14.5, 10.5; HRMS calcd for C$_{15}$H$_{16}$O$_3$+Na$^+$ 267.0997; found 267.0974 [M+Na$^+$].

1-(5-methylpyridin-2-yl)-ethanone (25)

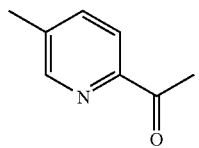

25

To a solution of 2-bromo-5-methylpyridine 23 (1.73 g, 10 mmol) in dry ether (20 ml), cooled to −78° C., was added n-butyllithium (6.25 ml of 1.6M solution in hexanes, 10 mmol, 1 equiv) dropwise. The reaction mixture was allowed to warm to −40° C. for 15 min, then cooled back to −78° C. again. N,N-dimethylacetamide (1.023 ml, 11 mmol, 1.1 equiv) was added dropwise and the mixture was stirred at −78° C. for 2 h. Saturated aqueous ammonium chloride (10 ml) was added and the organic layer was separated. The aqueous layer was extracted with ether (3×10 ml) and the combined organic layers were dried over anhydrous sodium sulfate, filtered, and concentrated in vacuo to give an oily residue that was subjected to flash column chromatography using (5% methanol in methylene chloride) to give compound 25 (0.977 g, 72%) as a yellow oil: TLC R$_f$=0.48 (silica gel, 25% EtOAc/hexanes); $^1$H NMR (400 MHz, CDCl$_3$) δ 8.5-8.48 (broad s, 1H), 7.94 (d, J=8.0 Hz, 1H), 7.63-7.60 (m, 1H), 2.70 (s, 3H), 2.41 (s, 3H); $^{13}$C NMR (75 MHz, CDCl$_3$) δ 200.2, 151.7, 149.7, 137.8, 137.4, 121.7, 26.0, 18.9; HRMS calcd for C$_8$H$_9$NO+Na$^+$ 158.0582; found 158.0580 [M+Na$^+$].

2-bromo-1-(5-methylpyridin-2-yl)ethanone (19b)

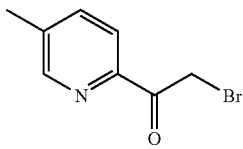

19b

To a solution of compound 25 (0.9 g, 6.67 mmol) in THF (25 ml) was added Amberlyst A26-Br$_3^−$ (Aldrich, 1.26 mmol Br$_3$/g) (4.76 g, 6 mmol, 0.9 equiv) in one portion. The mixture was stirred at 50° C. for 10 h and the decoloured resin was filtered off and washed with ethyl acetate. The organic solution was washed with water, dried over anhydrous sodium sulfate, and concentrated in vacuo to give an oily residue that was chromatographed on silica gel with (10-30% methylene chloride in hexanes) to give compound 19b (1.29 g, 91%) as an yellow oil: TLC R$_f$=0.62 (silica gel, 20% EtOAc/hexane); $^1$H NMR (400 MHz, CDCl$_3$) δ 8.50 (broad s, 1H), 8.01 (d, J=8.0 Hz, 1H), 7.66 (dd, J=1.6 Hz, 8.0 Hz, 1H), 4.84 (s, 2H), 2.44 (s, 3H); $^{13}$C NMR (75 MHz, CDCl$_3$) δ 192.5, 149.8, 149.3, 138.7, 137.6, 122.6, 32.5, 18.9; HRMS calcd for C$_8$H$_8$BrNO+Na$^+$ 235.9687; found 235.9676 [M+Na$^+$].

3-Oxo-2-(2-oxo-2-pyridin-2-yl-ethyl)-pentanoic acid ethyl ester (20b)

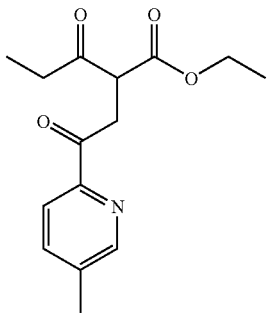

20b

Ethyl propionylacetate 18 (5 g, 34.7 mmol) was added slowly to a stirred suspension of sodium hydride (60% dispersion in mineral oil, 1.665 g, 41.65 mmol, 1.2 equiv) in THF (50 ml) at 0° C. and the mixture was stirred for 30 min. Compound 19b (8.092 g, 38.17 mmol, 1.1 equiv) in THF (5 ml) was added dropwise and the reaction mixture was stirred at room temperature for 16 h. Saturated aqueous ammonium chloride (30 ml) was added and the mixture was subsequently extracted with diethyl ether (3×30 ml). The combined organic layers were washed with brine and dried over anhydrous sodium sulfate. The solvent was removed in vacuo to give a dark yellow oil that was purified by flash column chromatography (10% EtOAc/hexanes) to give the diketoester 20b (7.3 g, 76%) as a yellow oil: TLC $R_f$=0.33 (silica gel, 20% EtOAc/hexane); $^1$H NMR (400 MHz, CDCl$_3$) δ 8.50 (broad s, 1H), 7.89 (d, J=8.0 Hz, 1H), 7.66 (dd, J=1.6 Hz, 8.0 Hz, 1H), 4.20 (q, J=7.2 Hz, 2H), 4.15 (dd, J=6.0 Hz, 8.0 Hz, 1H), 3.92 (dd, J=8.4 Hz, 18.8 Hz, 1H), 3.74 (dd, J=6.0 Hz, 18.8 Hz, 1H), 2.85-2.66 (m, 2H), 2.41 (s, 3H), 1.27 (t, J=7.2 Hz, 3H), 1.10 (t, J=7.2 Hz, 3H); $^{13}$C NMR (75 MHz, CDCl$_3$) δ 205.5, 198.9, 169.6, 150.7, 149.8, 138.1, 137.3, 121.7, 61.8, 53.5, 37.1, 36.2, 18.9, 14.2, 7.9; HRMS calcd for $C_{15}H_{19}NO_4+Na^+$ 300.1212; found 300.1200 [M+Na$^+$].

3-Methyl-2-oxo-4-pyridin-2-yl-cyclopent-3-enecarboxylic acid ethyl ester (21b)

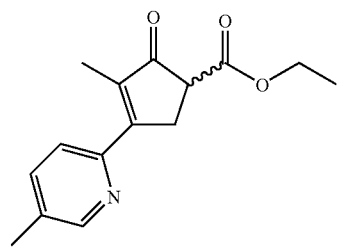

21b

A solution of the diketoester 20b (3.1 g, 11.19 mmol) in dry ethanol (35 ml) was added dropwise to a solution of sodium hydroxide (0.447 g, 11.19 mmol) in dry ethanol (15 ml) with vigorous stirring. The solution was stirred at room temperature overnight. Ether (200 ml) was added and the organic phase was washed with 2 N HCl (3×100 ml). The aqueous layer was cooled to 0° C. and made slightly basic by addition of sodium bicarbonate. The aqueous layer was then extracted with ethyl acetate (3×300 ml) and the organic phase was dried over anhydrous sodium sulfate. The solvent was removed in vacuo to give an oil that was purified by flash column chromatography (EtOAc/hexanes, 1:10) to give the cyclic β-ketoester 21b (2.115 g, 73%) as a yellow oil: TLC $R_f$=0.35 (silica gel, 33% EtOAc/hexanes); $^1$H NMR (400 MHz, CDCl$_3$) δ 8.59 (s, 1H), 7.62-7.60 (m, 1H), 7.54-7.52 (m, 1H), 4.24 (q, J=7.2 Hz, 2H), 3.56 (dd, J=2.8 Hz, 7.2 Hz, 1H), 3.42-3.25 (m, 2H), 2.41 (s, 3H), 2.12 (s, 3H), 1.31 (t, J=7.2 Hz, 3H); $^{13}$C NMR (75 MHz, CDCl$_3$) δ 203.2, 169.5, 164.4, 151.4, 150.6, 136.8, 136.5, 134.2, 123.3, 61.7, 51.1, 32.5, 18.6, 14.3, 10.6; HRMS calcd for $C_{15}H_{17}NO_3+Na^+$ 282.1106; found 282.1109 [M+Na$^+$].

(1R*,2S*,3E)-2-Hydroxy-3-methyl-4-phenyl-cyclopent-3-enecarboxylic acid ethyl ester (22a) and (ent-22a)

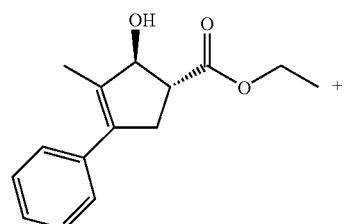

22a

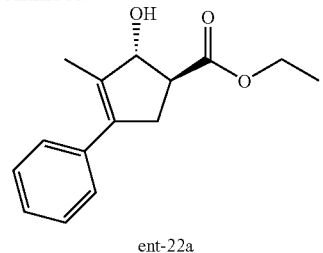

ent-22a

A solution of zinc borohydride (150 ml of 0.3M solution in ether, 45 mmol, 4 equiv) was added dropwise at 0° C. to a stirred solution of β-ketoester (+/−) 21a (2.75 g, 11.25 mmol) in THF (5 ml). The mixture was stirred overnight at 4° C., quenched by slow addition of water and stirred for an additional 1 hour. Anhydrous sodium sulfate was added and the resulting suspension was filtered and the filtrate was concentrated. The residue was dissolved in methylene chloride and filtered again and dried. Purification by flash column chromatography (8% EtOAc/hexanes) gave recovered starting material (0.27 g, 10%) and racemic β-hydroxyester 22a and ent-22a (2.1 g, 75%) as a yellow oil: TLC $R_f$=0.17 (silica gel, 25% EtOAc/hexanes); NMR (400 MHz, CDCl$_3$) δ 7.37-7.24 (m, 5H), 4.98 (s, 1H), 4.22 (q, J=7.2 Hz, 2H), 3.03-2.94 (m, 3H), 2.32 (d, J=5.6 Hz, 1H), 1.90 (s, 3H), 1.31 (t, J=7.2 Hz, 3H); $^{13}$C NMR (100 MHz, CDCl$_3$) δ 174.9, 137.2, 135.7, 135.1, 128.4, 127.9, 127.3, 83.9, 61.1, 51.8, 37.1, 14.5, 12.8; HRMS calcd for $C_{15}H_{18}O_3+Na^+$ 269.1154; found 269.1143 [M+Na$^+$].

(1R,2S,3E)-2-Acetoxy-3-methyl-4-phenyl-cyclopent-3-enecarboxylic acid ethyl ester (26) and (1R,2R,3E)-2-Hydroxy-3-methyl-4-phenyl-cyclopent-3-enecarboxylic acid ethyl ester (ent-22a)

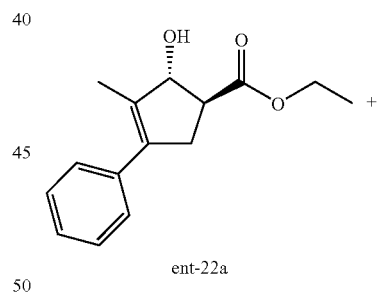

ent-22a

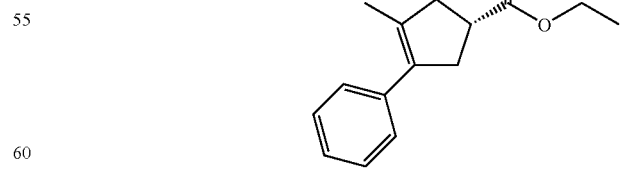

26

Vinyl acetate (7.5 ml, 81.4 mmol) was added to a solution of 22a and ent-22a (2 g, 8.13 mmol) in anhydrous pentane (30 ml). Amano PS-D lipase (2.0 g) and 4 Å MS (2.0 g) were added and the suspension was stirred at room temperature.

The reaction was monitored by TLC and ¹H NMR and after 4 days 48-50% conversion of 22a to the acetate was achieved. The sieves and lipase were filtered and washed with Et₂O. The solvent was removed and crude product was purified by flash column chromatography (20% ether/hexanes) to give 26 (1.15 g, 49%) as a slightly yellow oil and ent-22a (0.96 g, 48%, 98% ee).

Data for 26; $[\alpha]^{22}_D$=−50.5 (c=0.6, CHCl₃); TLC $R_f$=0.38 (silica gel, 25% EtOAc/hexanes); NMR (600 MHz, CDCl₃) δ 7.40-7.25 (m, 5H), 6.06 (s, 1H), 4.20 (q, J=7.2 Hz, 2H), 3.08-2.95 (m, 3H), 2.11 (s, 3H), 1.80 (s, 3H), 1.28 (t, J=7.2 Hz, 3H); ¹³C NMR (100 MHz, CDCl₃) δ 174.2, 170.9, 138.4, 136.7, 131.8, 128.5, 128.0, 127.7, 85.9, 61.2, 48.7, 38.6, 21.3, 14.4, 12.9; HRMS calcd for $C_{17}H_{20}O_4$+Na⁺ 311.1259; found 311.1240 [M+Na⁺].

Data for ent-22a; $[\alpha]^{22}_D$=−15.2 (c=0.6, CHCl₃); See 22a below for ¹H NMR and ¹³C data.

(1R,2S,3E)-2-Hydroxy-3-methyl-4-phenyl-cyclopent-3-enecarboxylic acid ethyl ester (22a)

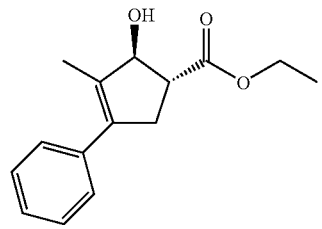

22a

Anhydrous potassium carbonate (240 mg, 1.74 mmol) was added at 0° C. to a solution of 26 (500 mg, 1.74 mmol) in dry ethanol (15 ml) and the solution was stirred at room temperature for 12 hr. Ethanol was removed under reduced pressure and the residue was dissolved in methylene chloride and washed with saturated aqueous solution of ammonium chloride. The organic phase was dried over anhydrous sodium sulfate and the solvent was removed in vacuo. The residue was purified by flash column chromatography (25% EtOAc/hexane) to give compound 22a (393 mg, 92%, 99% ee) as a slightly yellow oil: $[\alpha]^{22}_D$=+14.8 (c=0.8, CHCl₃); TLC $R_f$=0.17 (silica gel, 25% EtOAc/hexane); ¹H NMR (400 MHz, CDCl₃) δ 7.37-7.25 (m, 5H), 4.99 (s, 1H), 4.23 (q, J=7.2 Hz, 2H), 3.05-2.94 (m, 3H), 2.33 (d, J=5.6 Hz, 1H), 1.90 (s, 3H), 1.32 (t, J=7.2 Hz, 3H); ¹³C NMR (100 MHz, CDCl₃) δ 174.9, 137.2, 135.8, 135.1, 128.4, 127.9, 127.3, 84.0, 61.1, 51.7, 37.1, 14.5, 12.9; HRMS calcd for $C_{15}H_{18}O_3$+Na⁺ 269.1154; found 269.1148 [M+Na⁺].

(1R*,2S*,3E)-2-Hydroxy-3-methyl-4-pyridin-2-ylcyclopent-3-enecarboxylic acid ethyl ester (22b/ent-22b) and (27/ent-27)

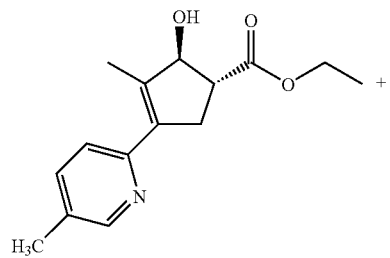

22b

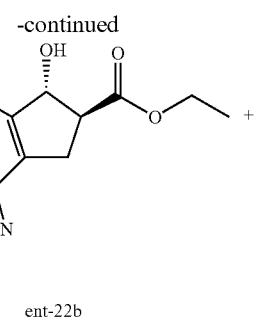

ent-22b

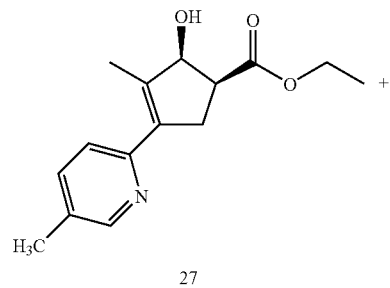

27

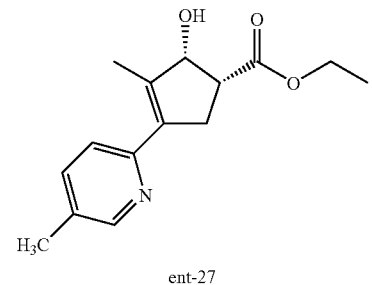

ent-27

Trifluoroacetic acid (0.297 ml, 3.86 mmol) was added to a stirred solution of compound 21b (0.5 g, 1.93 mmol) in methylene chloride (6 ml). The solvent was removed in vacuo. The resulting salt was dissolved in methanol (7 ml) and cooled to 0° C. To this solution at 0° C. was added sodium borohydride (0.73 g, 19.3 mmol) rapidly at once. After stirring at the same temperature for 30 min. chloroform was added and the mixture was washed with saturated sodium bicarbonate solution and brine. The organic layer was dried over anhydrous sodium sulfate and concentrated. The residue (0.459 g, 91%, cis/trans (1:2) by ¹H NMR) was separated using silica gel chromatography (16-25% EtOAc/hexane) to obtain 22b/ent-22b (0.306 g, 67%) and 27/ent-27 (0.153 g, 33%).

Data for 27/ent-27.

TLC $R_f$=0.29 (silica gel, 20% EtOAc/hexane); ¹H NMR (C₆D₆, 600 MHz): δ 8.38 (s, 1H), 6.88-6.87 (m, 2H), 4.61 (s, 1H), 3.99-3.89 (m, 2H), 3.54-3.49 (m, 1H), 3.05-3.01 (m, 1H), 2.88-2.84 (m, 1H), 2.33 (d, J=7.8 Hz, 1H), 2.13 (s, 3H), 1.77 (s, 3H), 0.90 (t, J=14.4, 3H); ¹³C NMR(C₆D₆, 400 MHz): δ 172.9, 153.5, 149.9, 138.6, 136.2, 135.9, 130.7, 121.9, 82.0, 60.4, 46.5, 36.2, 17.8, 14.1, 13.8. HRMS calcd for $C_{15}H_{19}NO_3$+$Na^+$ 284.1263; found 284.1248 (M+$Na^+$).

(1R,2S,3E)-2-Acetoxy-3-methyl-4-pyridin-2-yl-cyclopent-3-enecarboxylic acid ethyl ester (28) and (1R,2R,3E)-2-Hydroxy-3-methyl-4-pyridin-yl-cyclopent-3-enecarboxylic acid ethyl ester (ent-22b)

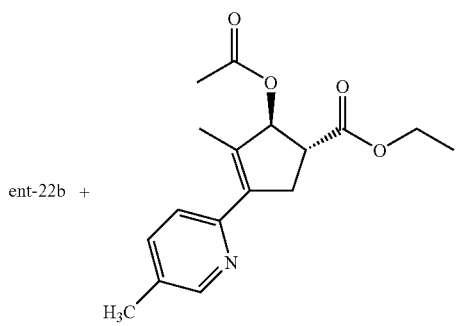

28

Vinyl acetate (0.95 ml, 10.3 mmol) was added to a solution of 22b/ent-22b (0.27 g, 1.03 mmol) in anhydrous pentane (3 ml). Amano PS-D lipase (0.27 g) and 4 Å MS (0.27 g) were added and the suspension was stirred at room temperature. The reaction was monitored by TLC and $^1$H NMR and after 3 days 49-50% conversion of 22b/ent-22b to acetate 28 was achieved. The sieves and lipase was filtered and washed with ether. The solvent was removed and the crude product was purified by column chromatography (17% EtOAc/hexane) to give 28 (0.154 g, 49%) as a pale yellow oil, and ent-22b (0.130 g, 48%)

Data for 28.

$[\alpha]^{20}_D$=−40.6 (c=1.0, CHCl$_3$); TLC $R_f$=0.26 (silica gel, 75% EtOAc/hexanes); $^1$H NMR (CDCl$_3$, 600 MHz) δ 8.44 (s, 1H), 7.47 (d, J=7.8 Hz, 1H), 7.20 (d, J=7.8 Hz, 1H), 6.07 (s, 1H), 4.19 (q, J=14.4 Hz, 2H), 3.22-3.16 (m, 1H), 3.05-3.01 (m, 2H), 2.32 (s, 3H), 2.09 (s, 3H), 1.94 (s, 3H), 1.26 (t, J=7.2 Hz, 3H); $^{13}$C NMR (CDCl$_3$, 400 MHz) δ 174.1, 170.9, 152.5, 150.0, 137.2, 136.7, 135.0, 137.8, 122.5, 85.9, 61.1, 48.5, 37.5, 21.3, 18.5, 14.4, 13.2. HRMS calcd for $C_{17}H_{21}NO_4$+$Na^+$ 326.1368; found 326.1354 (M+$Na^+$).

Data for ent-22b.

$[\alpha]^{20}_D$=+7.8 (c=1.0, CHCl$_3$). See 22b below for $^1$H NMR and $^{13}$C NMR data.

(1R,2S,3E)-2-Hydroxy-3-methyl-4-pyridin-2-ylcyclopent-3-enecarboxylic acid (22b)

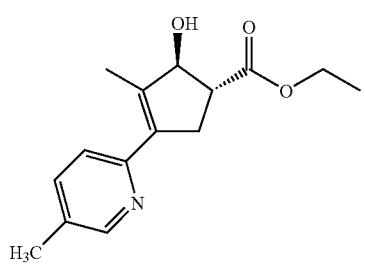

22b

Anhydrous potassium carbonate (45.6 mg, 0.33 mmol) was added at 0° C. to a solution of 28 (100 mg, 0.33 mmol) in dry ethanol (2.8 ml) and the solution was stirred at room temperature for 12 hr. Ethanol was removed under reduced pressure and the residue was dissolved in methylene chloride and washed with saturated aqueous solution of ammonium chloride. The organic phase was dried over anhydrous sodium sulfate and the solvent was removed in vacuo. The residue was purified by flash column chromatography (25% EtOAc/hexane) to give compound 22b (81 mg, 94%, 95% ee) as a pale yellow oil: $[\alpha]^{20}_D$=−8.1 (c=0.26, CHCl$_3$); TLC $R_f$=0.27 (silica gel, 75% EtOAc/hexanes); $^1$H NMR (C$_6$D$_6$, 600 MHz) δ 8.48 (s, 1H), 6.97-6.92 (m, 2H), 5.03 (s, 1H), 4.04-4.00 (m, 2H), 3.22-3.21 (m, 2H), 3.02-2.98 (m, 1H), 2.18 (s, 3H), 1.87 (s, 3H), 0.98 (t, J=14.4 Hz, 3H); $^{13}$C NMR (CDCl$_3$, 400 MHz) δ 174.6, 153.1, 149.9, 138.4, 136.7, 134.9, 131.4, 122.4, 84.1, 61.0, 51.7, 35.9, 18.5, 14.5, 13.1; HRMS calcd for $C_{15}H_{19}NO_3$+$Na^+$ 284.1263; found 284.1279 (M+$Na^+$).

(1R,2S,3E)-3-Methyl-4-phenyl-2-triethylsilanyloxy-cyclopent-3-enecarboxylic acid ethyl ester (29a)

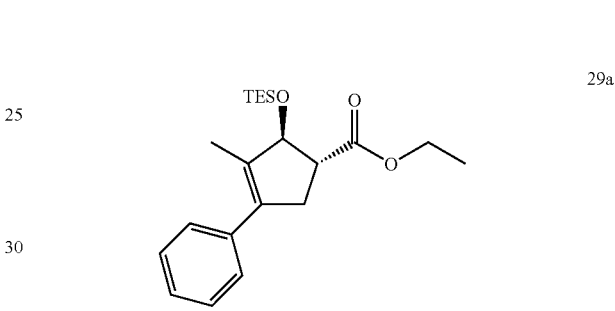

29a

Triethylsilyl chloride (876 µl, 5.22 mmol, 1.5 equiv) was added dropwise to a solution of alcohol 22a (856 mg, 3.48 mmol) and imidazole (711 mg, 10.44 mmol, 3 equiv) in methylene chloride (25 ml) at 0° C. After stirring at 0° C. for 2 hr, the reaction was quenched with water (15 ml), and extracted with ethyl acetate (3×30 ml). The organic extracts were washed with brine (20 ml), and dried over anhydrous sodium sulfate. Filtration and evaporation of the solvents in vacuo furnished an oily crude product which was purified by flash column chromatography (2% EtOAc/hexanes) to give TES ether 29a (1.16 g, 93%) as a yellow oil: $[\alpha]^{22}_D$=−34.2 (c=0.6, CHCl$_3$); TLC $R_f$=0.53 (silica gel, 10% EtOAc/hexanes); $^1$H NMR (400 MHz, CDCl$_3$) δ 7.36-7.22 (m, 5H), 5.11 (s, 1H), 4.21 (q, J=7.2 Hz, 2H), 3.08-2.82 (m, 3H), 1.83 (s, 3H), 1.32 (t, J=7.2 Hz, 3H), 1.00 (t, J=8.0 Hz, 9H), 0.68 (q, J=8.0 Hz, 6H); $^{13}$C NMR (75 MHz, CDCl$_3$) δ 175.5, 137.5, 135.7, 134.9, 128.3, 128.0, 127.2, 84.5, 60.9, 51.8, 38.6, 14.5, 12.9, 7.1, 5.1, 0.2; HRMS calcd for $C_{21}H_{32}O_3Si$+$Na^+$ 383.2018; found 383.2019 [M+$Na^+$].

(1R,2S,3E)-3-Methyl-4-phenyl-2-triethylsilanyloxy-cyclopent-3-enecarbaldehyde (30a)

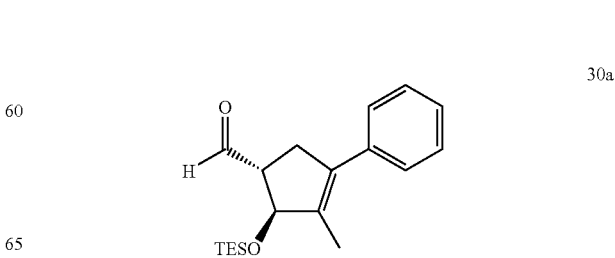

30a

A solution of DIBAL-H (2.2 ml, 1.0 M in hexane, 2.2 mmol, 1.1 equiv) was added dropwise to a solution of silyl ether 29a (720 mg, 2 mmol) in toluene (10 ml) at −78° C. The reaction was stirred at that temperature for 1 h and quenched by dropwise addition of saturated NH$_4$Cl (1.0 ml). The reaction was allowed to reach room temperature and a saturated solution of Rochelle salt (3.0 ml) and brine (2.0 ml) were added. The mixture was extracted with ethyl acetate (3×7 ml) and the combined organic extracts were dried over anhydrous sodium sulfate, filtered, and evaporated in vacuo to give crude aldehyde 30a as a colorless liquid which was used in the next step without further purification; $^1$H NMR (400 MHz, CDCl$_3$) δ 9.86 (d, J=2.0 Hz, 1H), 7.38-7.25 (m, 5H), 5.08 (s, 1H), 3.12-2.98 (m, 2H), 2.90-2.84 (m, 1H), 1.84 (s, 3H), 1.00 (t, J=8.0 Hz; 9H), 0.68 (q, J=8.0 Hz, 6H); $^{13}$C NMR (75 MHz, CDCl$_3$) δ 200.2, 135.5, 133.9, 133.7, 126.6, 126.3, 125.6, 79.6, 57.4, 33.1, 11.3, 5.3, 3.4.

(1S,2E,5S)-Triethyl-(2-methyl-3-phenyl-5-vinyl-cyclopent-2-enyloxy)-silane (31a)

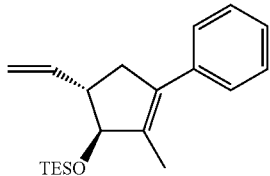

31a

To a pre-cooled (0° C.) solution of methyltriphenylphosphonium bromide (455 mg, 1.27 mmol, 2 equiv) in THF (5 ml) was added n-butyllithium (0.775 ml of 1.6 M solution in hexanes, 1.24 mmol, 1.95 equiv) dropwise. The reaction mixture was stirred at 0° C. for 30 min. A solution of aldehyde 30a (0.2 g, 0.633 mmol) in THF (2 ml) was added and the mixture was stirred at 0° C. for 30 min and quenched with a saturated aqueous ammonium chloride (5 ml). The solvent was removed under reduced pressure, and the aqueous residue was extracted with ethyl acetate (3×5 ml). The combined organic extract was dried over anhydrous sodium sulfate and concentrated in vacuo. Purification by flash column chromatography (5% ether/hexanes) afforded pure olefin 31a (0.14 g, 71%) as a colorless oil: [α]$^{22}$$_D$=−14.3 (c=0.4, CHCl$_3$); TLC R$_f$=0.73 (silica gel, 10% ether/hexanes); $^1$H NMR (600 MHz, CDCl$_3$) δ 7.34-7.21 (m, 5H), 5.94-5.88 (m, 1H), 5.12 (d, J=16.8 Hz, 1H), 5.04 (dd, J=1.8 Hz, 10.2 Hz, 1H), 4.52 (d, J=4.8 Hz, 1H), 2.88-2.82 (m, 1H), 2.74-2.68 (m, 1H), 2.52-2.47 (m, 1H), 1.82 (s, 3H), 0.98 (t, J=7.8 Hz, 9H), 0.66 (q, J=7.8 Hz, 6H); $^{13}$C NMR (100 MHz, CDCl$_3$) δ 141.1, 138.1, 136.3, 135.7, 128.3, 127.9, 126.9, 115.2, 87.0, 52.1, 40.4, 13.1, 7.2, 5.5; HRMS calcd for C$_{20}$H$_{30}$OSi+Na$^+$ 337.1964 found 337.1970 [M+Na$^+$].

(1S,2E,5S)-2-Methyl-3-phenyl-5-vinyl-cyclopent-2-enol (5a)

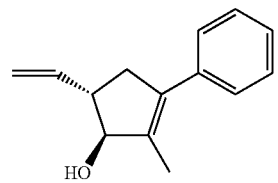

5a

To a solution of compound 31a (0.48 g, 1.53 mmol) in THF (7 ml) at 0° C. was added tetrabutylammonium fluoride (1.53 ml of 1 M solution in THF, 1.53 mmol) dropwise. The reaction mixture was stirred at 0° C. for 30 min and then water (6 ml) and ethyl acetate (10 ml) were added. The layers were separated and the aqueous layer was extracted with ethyl acetate (2×10 m). The combined organic layers were dried over anhydrous sodium sulfate and concentrated in vacuo. Purification by flash column chromatography (10% EtOAc/hexanes) afforded pure alcohol 5a (0.245 g, 80%) as a white solid: [α]$^{22}$$_D$=−14.17 (c=1.2, CHCl$_3$); TLC R$_f$=0.45 (silica gel, 33% EtOAc/hexanes); $^1$H NMR (600 MHz, CDCl$_3$) δ 7.36-7.23 (m, 5H), 6.00-5.94 (m, 1H), 5.18 (dd, J=1.2 Hz, 16.8 Hz, 1H), 5.08 (dd, J=0.6 Hz, 10.2 Hz, 1H), 4.48 (d, J=6.6 Hz, 1H), 2.85-2.81 (m, 1H), 2.71-2.65 (m, 1H), 2.59-2.54 (m, 1H), 1.89 (s, 3H); $^{13}$C NMR (100 MHz, CDCl$_3$) δ 140.4, 137.8, 136.3, 135.9, 128.4, 127.9, 127.2, 115.4, 86.4, 52.4, 39.8, 12.9; HRMS calcd for C$_{14}$H$_{16}$O+Na$^+$ 223.1099; found 223.1100 [M+Na$^+$].

(1R,2S)-3-Methyl-4-(5-methyl-pyridin-2-yl)-2-triethylsilanyloxy-cyclopent-3-enecarboxylic acid ethyl ester (29b)

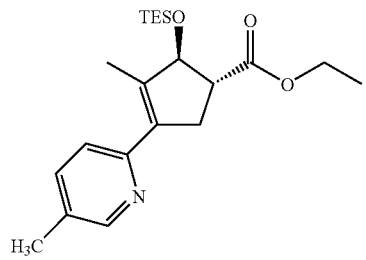

29b

Triethylsilyl chloride (145 μL, 0.863 mmol, 1.5 equiv) was added dropwise to a solution of alcohol 22b (150 mg, 0.575 mmol) and imidazole (17 mg, 1.72 mmol, 3 equiv) in methylene chloride (4 ml) at 0° C. After stirring at 0° C. for 2 hr, the reaction was quenched with water (2.5 ml), and extracted with ethyl acetate (3×5 ml). The organic extracts were washed with brine (3.5 ml), and dried over anhydrous sodium sulfate. Filtration and evaporation of the solvents in vacuo furnished an oily crude product which was purified by flash column chromatography on silica (2-7% EtOAc/hexanes-) to give 29b (198 mg, 92%) as a yellow oil: [α]$^{22}$$_D$=−51.04 (c=0.7, CHCl$_3$); TLC R$_f$=0.29 (silica gel, 25% EtOAc/hexanes); $^1$H NMR (600 MHz, CDCl$_3$) δ 8.41 (s, 1H), 7.44 (dd, J=1.8 Hz, 8.4 Hz, 1H), 7.19 (d, J=7.8 Hz, 1H), 5.12 (d, J=4.8 Hz, 1H), 4.18 (dd, J=7.2 Hz, 14.4 Hz, 2H), 3.17-3.12 (m, 1H), 3.0-2.89 (m, 2H), 2.30 (s, 3H), 1.97 (s, 3H), 1.28 (t, J=14.4 Hz, 3H), 0.96 (t, J=7.8 Hz, 9H), 0.65 (q, J=7.8 Hz, 6H); $^{13}$C NMR (100 MHz, CDCl$_3$) δ 175.3, 153.3, 149.9, 139.1, 136.5, 134.1, 131.1, 122.4, 84.5, 60.8, 51.6, 37.4, 18.4, 14.5, 13.3, 7.0, 5.2; HRMS calcd for $C_{21}H_{33}NO_3Si+H^+$ 376.2308; found 376.2302 [M+H$^+$].

(1R,2S)-3-Methyl-4-pyridin-2-yl-2-triethylsilanyloxy-cyclopent-3-enecarbaldehyde (30b)

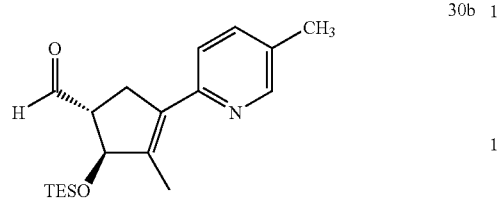

A solution of DIBAL-H (0.44 ml, 1.0 M in hexane, 0.44 mmol, 1.1 equiv) was added dropwise to a solution of silyl ether 29b (150 mg, 0.4 mmol) in toluene (2 ml) at −78° C. The reaction mixture was stirred at that temperature for 1 hr and quenched by dropwise addition of saturated NH$_4$Cl solution (0.2 ml). The reaction mixture was allowed to reach room temperature and a saturated solution of Rochelle salt (1 ml) and brine (0.4 ml) were added. The mixture was extracted with ethyl acetate (3×2 ml) and the combined organic extracts were dried over anhydrous sodium sulfate, filtered, and evaporated in vacuo to give crude aldehyde 30b as a yellow liquid which was used in the next step without further purification.

(3S,4S)-5-Methyl-2-(2-methyl-3-triethylsilanyloxy-4-vinyl-cyclopent-1-enyl)-pyridine (31b)

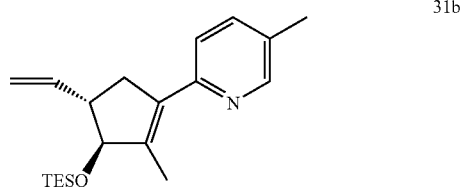

To a pre-cooled (0° C.) solution of methyltriphenylphosphonium bromide (286 mg, 0.8 mmol, 2 equiv) in THF (3 ml) was added n-butyllithium (0.49 ml of 1.6 M solution in hexanes, 0.78 mmol, 1.95 equiv) dropwise. The reaction mixture was stirred at 0° C. for 30 min. A solution of crude aldehyde 30b (ca 0.4 mmol) in THF (1.5 ml) was added and the mixture was stirred at 0° C. for 30 min and quenched with a saturated aqueous ammonium chloride solution (3 ml). The solvent was removed under reduced pressure, and the aqueous residue was extracted with ethyl acetate (3×3 ml). The combined organic extracts were dried over anhydrous sodium sulfate and concentrated in vacuo. Purification by flash column chromatography on silica (7% EtOAc/hexanes) afforded pure olefin 31b (96 mg, 73%) as a yellowish oil: $[\alpha]^{22}_D$=−21.29 (c=0.7, CHCl$_3$); TLC R$_f$=0.66 (silica gel, 33% EtOAc/hexanes); $^1$H NMR (600 MHz, CDCl$_3$) δ 8.42 (s, 1H), 7.44 (dd, J=1.8 Hz, 7.8 Hz, 1H), 7.18 (d, J=7.8 Hz, 1H), 5.95-5.88 (m, 1H), 5.12 (d, J=16.8 Hz, 1H), 5.04 (d, J=10.8 Hz, 1H), 4.54 (d, J=5.4 Hz, 1H), 2.97-2.93 (m, 1H), 2.74-2.68 (m, 1H), 2.60-2.56 (m, 1H), 2.30 (s, 3H), 1.96 (s, 3H), 0.98 (t, J=7.8 Hz, 9H), 0.64 (q, J=7.8 Hz, 6H); $^{13}$C NMR (100 MHz, CDCl$_3$) δ 153.9, 149.8, 140.9, 139.8, 136.5, 135.0, 130.9, 122.4, 115.2, 87.2, 51.8, 39.2, 18.4, 13.4, 7.2, 5.5; HRMS calcd for $C_{20}H_{31}NOSi+H^+$ 330.2253 found 330.2258 [M+H$^+$].

(1S,5S)-2-Methyl-3-(5-methylpyridin-2-yl)-5-vinyl-cyclopent-2-enol (5b)

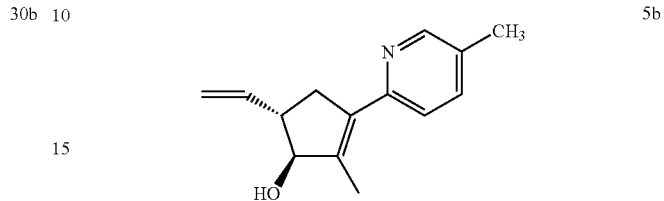

To a solution of compound 31b (50 mg, 0.152 mmol) in THF (1 ml) at 0° C. was added tetrabutylammonium fluoride (0.152 ml of 1 M solution in THF, 0.152 mmol) dropwise. The reaction mixture was stirred at 0° C. for 30 min and water (1 ml) and ethyl acetate (2 ml) were added. The layers were separated and the aqueous layer was extracted with ethyl acetate (2×2 ml). The combined organic layers were dried over anhydrous sodium sulfate and concentrated in vacuo. Purification by flash column chromatography on silica (16-50% EtOAc/hexanes) afforded pure alcohol 5b (28 mg, 83%) as a white solid: $[\alpha]^{22}_D$=−26.0 (c=0.3, CHCl$_3$); TLC R$_f$=0.25 (silica gel, 50% EtOAc/hexanes); $^1$H NMR (600 MHz, CDCl$_3$) δ 8.43 (s, 1H), 7.46 (dd, J=1.8 Hz, 7.8 Hz, 1H), 7.18 (d, J=7.8 Hz, 1H), 6.0-5.95 (m, 1H), 5.14 (d, J=16.8 Hz, 1H), 5.08 (d, J=10.2 Hz, 1H), 4.48 (s, 1H), 2.96-2.91 (m, 1H), 2.69-2.60 (m, 2H), 2.32 (s, 3H), 2.03 (s, 3H); $^{13}$C NMR (100 MHz, CDCl$_3$) δ 153.6, 149.9, 140.2, 139.4, 136.7, 135.6, 131.2, 122.3, 115.4, 86.4, 52.3, 38.5, 18.5, 13.2; HRMS calcd for $C_{14}H_{17}NO+Na^+$ 238.1208; found 238.1191 [M+Na$^+$].

(3S,6R,7S,8S)-3-(tert-Butyl-dimethyl-silanyloxy)-4,4,6,8,12-pentamethyl-5-oxo-7-(2,2,2-trichloro-ethoxycarbonyloxy)-tridec-12-enoic acid-(1S,2E,5S)-2-methyl-3-phenyl-5-vinyl-cyclopent-2-enyl ester (32a)

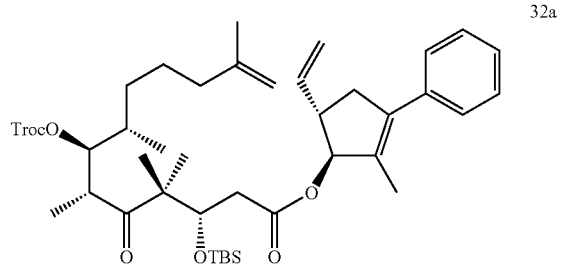

To a solution of acid 17 (13 mg, 0.021 mmol), alcohol 5a (4.6 mg, 0.023 mmol, 1.1 equiv), and DMAP (1 mg, 0.008 mmol, 0.4 equiv) in methylene chloride (0.5 ml) at 0° C. was added DCC (0.027 ml of 1 M solution in CH$_2$Cl$_2$, 0.027 mmol, 1.3 equiv) dropwise. The reaction mixture was stirred for 15 min at 0° C. and for 16 h at room temperature. The solid precipitate was filtered off and the filtrate was concentrated in vacuo. Purification by flash column chromatography (5% ether/hexanes) afforded ester 32a (11 mg, 64%) as a colorless oil: $[\alpha]^{22}{}_D = -53.2$ (c=0.85, CHCl$_3$); TLC R$_f$=0.67 (silica gel, 25% EtOAc/hexanes); $^1$H NMR (600 MHz, CDCl$_3$) δ 7.36-7.25 (m, 5H), 5.98-5.91 (m, 1H), 5.70 (d, J=4.2 Hz, 1H), 5.10 (d, J=17.4 Hz, 1H), 5.03 (d, J=10.2 Hz, 1H), 4.88-4.85 (m, 1H), 4.70 (dd, J=3 Hz, 8.4 Hz, 1H), 4.66-4.60 (m, 3H), 4.29 (t, J=4.2 Hz, 1H), 3.50-3.46 (m, 1H), 2.96-2.92 (m, 1H), 2.86-2.81 (m, 1H), 2.68 (dd, J=3.6 Hz, 17.4 Hz, 1H), 2.59-2.55 (m, 1H), 2.23 (dd, J=5.4 Hz, 17.4 Hz, 1H), 1.95-1.87 (m, 2H), 1.75 (s, 3H), 1.66 (s, 3H), 1.54-1.53 (m, 6H), 1.33-1.27 (m, 5H), 1.06-1.04 (m, 3H), 0.96 (d, J=6.6 Hz, 3H), 0.87 (s, 9H), 0.13 (s, 3H), 0.05 (s, 3H); $^{13}$C NMR (100 MHz, CDCl$_3$) δ 215.4, 172.3, 154.4, 145.8, 139.3, 137.3, 132.4, 128.4, 127.9, 127.4, 115.3, 110.3, 95.0, 88.2, 82.4, 76.9, 75.0, 56.0, 54.0, 47.6, 42.2, 40.5, 40.3, 38.2, 35.2, 34.9, 31.8, 31.2, 26.2, 25.7, 24.9, 24.8, 22.7, 22.6, 20.6, 18.4, 16.1, 13.1, 11.1, -4.1, -4.5; HRMS calcd for C$_{41}$H$_{61}$Cl$_3$O$_7$Si+Na$^+$ 821.3150; found 821.3178 [M+Na$^+$].

(3S,6R,7S,8S)-3,7-Dihydroxy-4,4,6,8,12-pentamethyl-5-oxo-tridec-12-enoic acid-(1S,2E,5S)-2-methyl-3-phenyl-5-vinyl-cyclopent-2-enyl ester (2a)

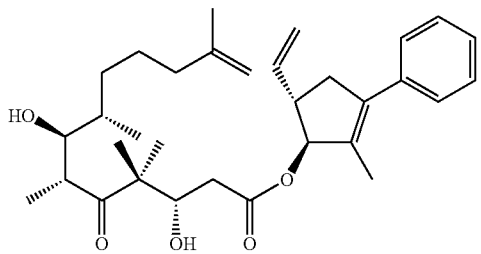

2a

To a solution of ester 32a (12 mg, 0.015 mmol) in dry ethanol (1.5 ml) was added anhydrous ammonium chloride (75 mg) followed by zinc dust (75 mg). The reaction mixture was stirred at room temperature for 45 min before it was diluted with ethyl acetate (5 ml) and filtered though a plug of celite. The solution was concentrated and passed though a small plug of silica gel to give compound 33 that was used in the next step without further purification. To the crude solution of compound 33 was added a solution of tris(dimethylamino)sulfur (trimethylsilyl)difluoride (TAS-F) (5 mg, 0.187 mmol, 1 equiv) in 0.2 ml N,N-dimethylforamide. After 24 h, another 5 mg of TAS-F was added and the mixture was stirred for additional 24 h after which it was diluted with ethyl acetate (5 ml) and washed with pH 7 buffer (5 ml). The aqueous layer was extracted with ethyl acetate (3×5 ml) and the combined organic layers were dried over anhydrous sodium sulfate, filtered, and concentrated in vacuo. The crude oil was purified by silica gel chromatography (10% EtOAc/hexanes) to give pure compound 2a (4.7 mg, 62% over two steps) as a colorless material: $[\alpha]^{22}{}_D = -77.5$ (c=0.2, CHCl$_3$); TLC R$_f$=0.74 (silica gel, 50% EtOAc/hexanes); $^1$H NMR (600 MHz, CDCl$_3$) δ 7.37-7.25 (m, 5H), 6.0-5.92 (m, 1H), 5.76 (d, J=3.6 Hz, 1H), 5.13 (d, J=16.8 Hz, 1H), 5.06 (d, J=10.2 Hz, 1H), 4.66 (d, J=10.2 Hz, 2H), 4.29-4.26 (m, 1H), 3.39-3.35 (m, 2H), 3.27-3.23 (m, 2H), 2.99-2.93 (m, 1H), 2.88-2.83 (m, 1H), 2.61-2.57 (m, 1H), 2.52 (dd, J=1.8 Hz, 16.2 Hz, 1H), 2.44 (dd, J=10.2 Hz, 16.2 Hz, 1H), 2.04-1.96 (m, 2H), 1.79 (s, 3H), 1.75-1.72 (m, 1H), 1.69 (s, 3H), 1.54-1.52 (m, 1H), 1.36-1.30 (m, 1H), 1.20-1.18 (s overlapping with m, 4H), 1.15 (s, 3H), 1.06 (d, J=7.2 Hz, 3H), 0.84 (d, J=7.2 Hz, 3H); $^{13}$C NMR (100 MHz, CDCl$_3$) δ 222.5, 173.2, 146.4, 139.8, 139.4, 137.1, 131.8, 128.5, 127.9, 127.6, 115.5, 109.9, 88.6, 75.0, 72.7, 52.3, 47.8, 41.1, 40.4, 38.4, 36.9, 35.7, 32.7, 25.0, 22.6, 21.5, 19.2, 15.7, 13.1, 10.2; HRMS calcd for C$_{32}$H$_{46}$O$_5$+Na$^+$ 533.3243; found 533.3213 [M+Na$^+$].

2E,4S,7S,10R,11S,12S,16Z,18S)-7,11-Dihydroxy-3,8,8,10,12,16-hexamethyl-2-phenyl-3a,7,8,10,11,12,13,14,15,17a-decahydro-1H,6H-4-oxa-cyclopentacyclohexadecene-5,9-dione (1a)

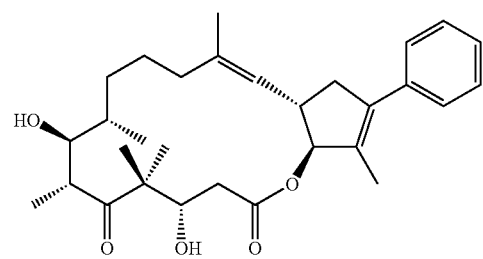

1a

A solution of the second generation Grubbs' catalyst (1.5 mg, 0.0018 mmol) (weighed under argon) in methylene chloride (1.5 ml) was added to a solution of compound 2a (1.5 mg, 0.0032 mmol) in methylene chloride (0.5 ml). The reaction mixture was heated at 50° C. for 16 h and applied directly to a preparative TLC (3:1 hexanes/EtOAc) to give the target Z 1a and slightly impure E (0.2 mg) separately (~50% overall yield). The Z isomer was purified by a second preparative TLC using (3% methanol/methylene chloride) to remove the last traces of the catalyst and to furnish the desired target molecule Z 1a (0.5 mg). $^1$H NMR (600 MHz, CDCl$_3$) δ 7.36-7.33 (m, 2H), 7.27-7.24 (m, 3H), 5.82 (d, J=7.2 Hz, 1H), 5.24 (d, J=10.2 Hz, 1H), 4.2-4.17 (m, 1H), 3.69-3.66 (m, 1H), 3.22-3.15 (m, 2H), 2.81 (dd, J=8.4 Hz, 15.6 Hz, 1H), 2.66 (d, J=4.2 Hz, 1H), 2.58 (dd, J=10.8 Hz, 16.8 Hz, 2H), 2.52-2.47 (m, 1H), 2.39-2.31 (m, 2H), 1.80-1.75 (s overlapping with m, 4H), 1.68 (s, 3H), 1.66-1.62 (m, 3H), 1.36 (s, 3H), 1.18 (d, J=6.6 Hz, 3H), 1.07 (s, 3H), 0.98 (d, J=7.2 Hz, 3H); HRMS calcd for C$_{30}$H$_{42}$O$_5$+Na$^+$ 505.2930; found 505.2893 [M+Na$^+$].

(3S,6R,7S,8S,1'S,5'S)-3-(tert-Butyl-dimethyl-silanyloxy)-4,4,6,8,12-pentamethyl-5-oxo-7-(2,2,2-trichloro-ethoxycarbonyloxy)-tridec-12-enoic acid 2-methyl-3-(5-methyl-pyridin-2-yl)-5-vinyl-cyclopent-2-enyl ester (32b)

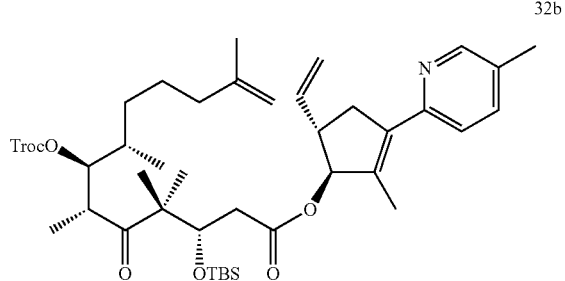

32b

To a solution of acid 17 (8.0 mg, 0.013 mmol), alcohol 5b (3.0 mg, 0.014 mmol, 1.1 equiv), and DMAP (1 mg, 0.008 mmol, 0.6 equiv) in methylene chloride (0.5 ml) at 0° C. was added DCC (0.017 ml of 1 M solution in CH$_2$Cl$_2$, 0.017 mmol, 1.3 equiv) dropwise. The reaction mixture was stirred for 15 min at 0° C. and for 16 h at room temperature. The solid precipitate was filtered off and the filtrate was concentrated in vacuo. Purification by flash column chromatography on silica (5% EtOAc/hexanes) afforded ester 32b (9 mg, 85%) as a colorless oil: [α]$^{22}_D$=−29.8 (c=1, CHCl$_3$); TLC R$_f$=0.48 (silica gel, 25% EtOAc/hexanes); $^1$H NMR (600 MHz, CDCl$_3$) δ 8.43 (s, 1H), 7.46 (dd, J=1.8 Hz, 7.8 Hz, 1H), 7.18 (d, J=7.8 Hz, 1H), 5.98-5.91 (m, 1H), 5.73 (d, J=4.8 Hz, 1H), 5.11 (d, J=16.8 Hz, 1H), 5.02 (d, J=10.2 Hz, 1H), 4.86 (d, J=12.0 Hz, 1H), 4.73-4.70 (m, 1H), 4.67-4.61 (m, 3H), 4.30-4.28 (m, 1H), 3.50-3.45 (m, 1H), 3.06-3.02 (m, 1H), 2.88-2.83 (m, 1H), 2.70-2.65 (m, 1H), 2.33 (s, 3H), 2.23 (dd, J=5.4 Hz, 17.4 Hz, 1H), 1.98-1.91 (m, 2H), 1.95 (s, 3H), 1.76-1.74 (m, 1H), 1.66 (s, 3H), 1.50-1.22 (m, 5H), 1.10-1.04 (m, 6H), 0.96 (d, J=7.2 Hz, 3H), 0.87 (m, 12H), 0.13 (s, 3H), 0.05 (s, 3H); $^{13}$C NMR (100 MHz, CDCl$_3$) δ 215.4, 172.3, 154.4, 153.1, 149.9, 145.8, 139.5, 138.3, 136.7, 135.7, 131.5, 125.5, 122.5, 115.4, 110.3, 95.0, 88.2, 82.4, 75.0, 54.0, 47.5, 42.2, 40.2, 39.2, 38.2, 34.9, 31.8, 29.9, 26.3, 24.8, 22.6, 22.5, 20.7, 18.5, 18.4, 16.1, 13.4, 11.1, −4.1, −4.5; HRMS calcd for C$_{41}$H$_{62}$Cl$_3$NO$_7$Si+H$^+$ 814.3434; found 814.3481 [M+H$^+$].

(3S,6R,7S,8S,1'S,5'S)-3,7-Dihydroxy-4,4,6,8,12-pentamethyl-5-oxo-tridec-12-enoic acid 2-methyl-3-(5-methyl-pyridin-2-yl)-5-vinyl-cyclopent-2-enyl ester (2b)

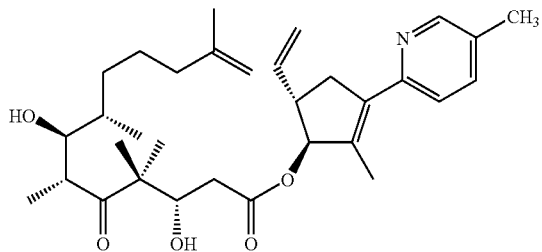

2b

To a solution of ester 32b (5 mg, 0.006 mmol) in DMF (0.2 ml) was added a solution of tris(dimethylamino)sulfur (trimethylsilyl)difluoride (TAS-F) (1.7 mg, 0.008 mmol, 1 equiv) in 0.2 ml N,N-dimethylforamide. After 24 h, another 1.7 mg of TAS-F was added and the mixture was diluted with ethyl acetate (3 ml) and washed with pH 7 buffer (5 ml). The aqueous layer was extracted with ethyl acetate (3×5 ml) and the combined organic layers were dried over anhydrous sodium sulfate, filtered, and concentrated in vacuo. The crude oil was purified by silica gel chromatography (10% EtOAc/hexanes) to give compound 34 which was dissolved in dry ethanol (1.2 ml) and treated with anhydrous ammonium chloride (62 mg) followed by zinc dust (62 mg). The reaction mixture was stirred at room temperature for 45 min before it was diluted with ethyl acetate (3 ml) and filtered though a plug of celite. The solution was concentrated and purified by silica gel chromatography (20% EtOAc/hexanes) to give pure compound 2b (2 mg, 62% over two steps) as a colorless material: TLC R$_f$=0.36 (silica gel, 33% EtOAc/hexanes).

Figure 16:
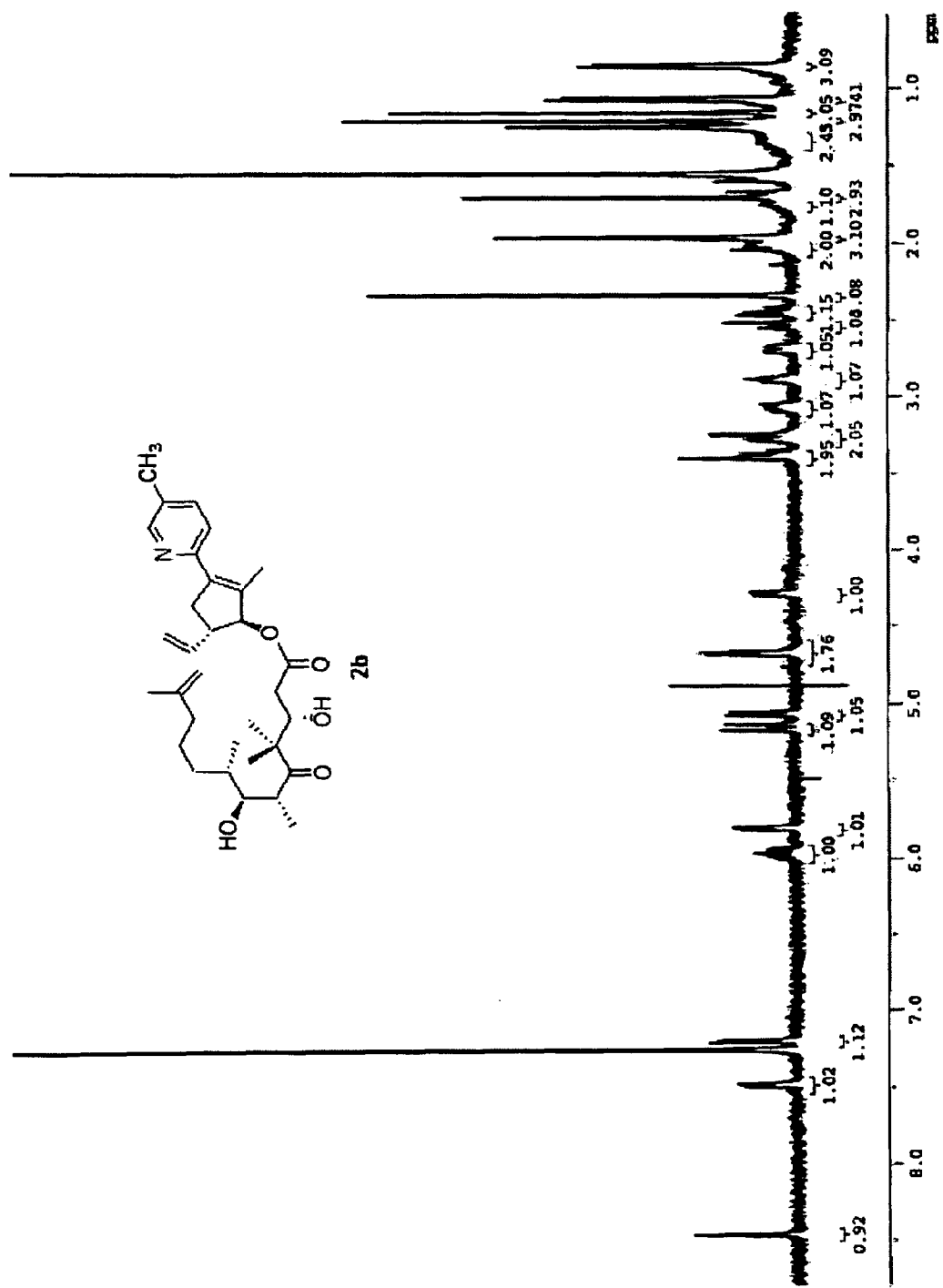
FIG. 16 shows the $^1$H NMR spectra for 2b.

FIG. 16 shows $^1$H NMR (500 MHz, CDCl$_3$) δ 8.47 (s, 1H), 7.50 (d, J=8.0 Hz, 1H), 7.21 (d, J=8.5 Hz, 1H), 6.02-5.95 (m, 1H), 5.81 (d, J=4.5 Hz, 1H), 5.16 (d, J=17.5 Hz, 1H), 5.07 (d, J=10.5 Hz, 1H), 4.68 (d, J=9.0 Hz, 2H), 4.30 (d, J=10.5 Hz, 1H), 3.41-3.37 (m, 2H), 3.30-3.27 (m, 1H), 3.25 (d, J=3.5 Hz, 1H), 3.10-3.3.06 (m, 1H), 2.91-2.88 (m, 1H), 2.71-2.69 (m, 1H), 2.54 (dd, J=2.5 Hz, 16.5 Hz, 1H), 2.46 (dd, J=10.5 Hz, 16.5 Hz, 1H), 2.35 (s, 3H), 2.06-2.02 (m, 2H), 1.98 (s, 3H), 1.78-1.76 (m, 1H), 1.72 (s, 3H), 1.33-1.31 (m, 2H), 1.22 (s, 3H), 1.17 (s, 3H), 1.08 (d, J=6.5 Hz, 3H), 0.87 (d, J=7.0 Hz, 3H).

Figure 17:
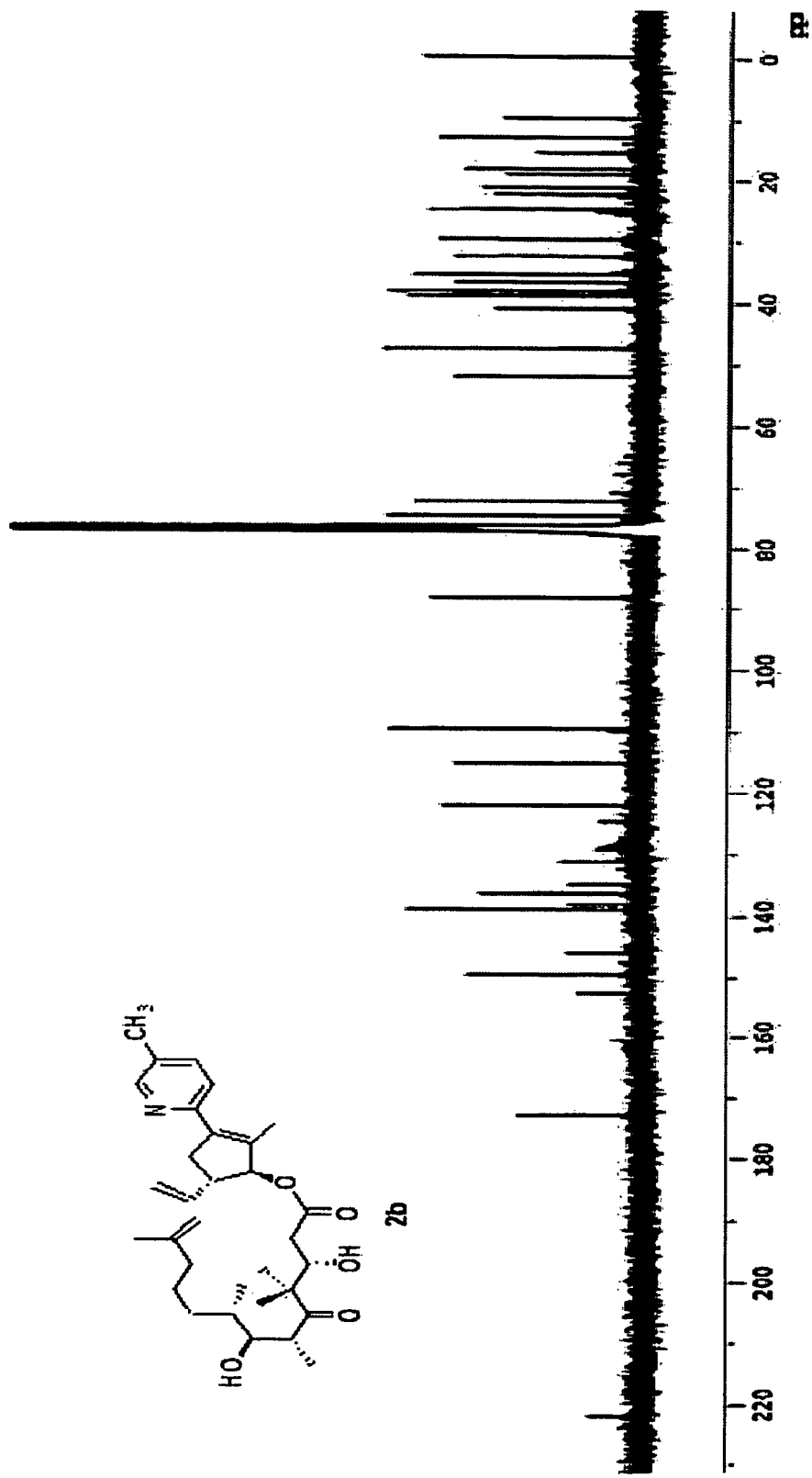
FIG. 17 shows the $^{13}$C NMR spectra for 2b.

FIG. 17 shows $^{13}$C NMR (125 MHz, CDCl$_3$) δ 222.1, 172.9, 152.8, 149.8, 146.2, 139.1, 136.5, 135.0, 131.4, 122.2, 115.3, 109.7, 88.3, 74.9, 72.5, 52.1, 47.5, 41.0, 38.9, 38.2, 36.8, 35.5, 32.5, 29.7, 24.9, 22.4, 21.3, 19.0, 18.3, 15.6, 13.2, 10.0; HRMS calcd for C$_{32}$H$_{47}$NO$_5$+Na$^+$ 548.3352; found 548.3331 [M+Na$^+$].

(3S,6R,7S,8S,1'S,5'S)-7,11-Dihydroxy-3,8,8,10,12,16-hexamethyl-2-(5-methyl-pyridin-2-yl)-3a,7,8,10,11,12,13,14,15,17a-decahydro-1H,6H-4-oxa-cyclopentacyclohexadecene-5,9-dione (1b)

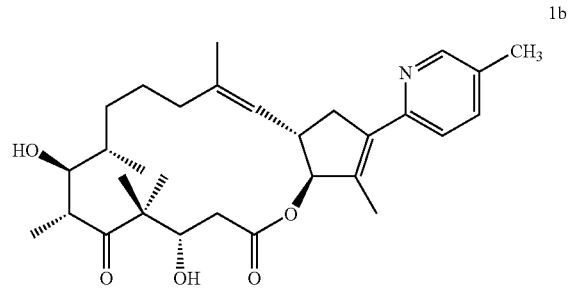

1b

A solution of the second generation Grubbs' catalyst (2.5 mg, 0.003 mmol) (weighed under argon) in methylene chloride (1.5 ml) was added to a solution of compound 2b (2.5 mg, 0.0052 mmol) in methylene chloride (0.5 ml). The reaction mixture was heated at 50° C. for 16 h and applied directly to a preparative TLC (3:1 hexanes/EtOAc) to give the target Z 1b (0.5 mg) a long with phenyl analogue 35 and the dimer 36 (~0.5 mg each) (~55 overall yield). Data for compound 1b; TLC R$_f$=0.23 (silica gel, 50% EtOAc/hexanes)

Figure 18:
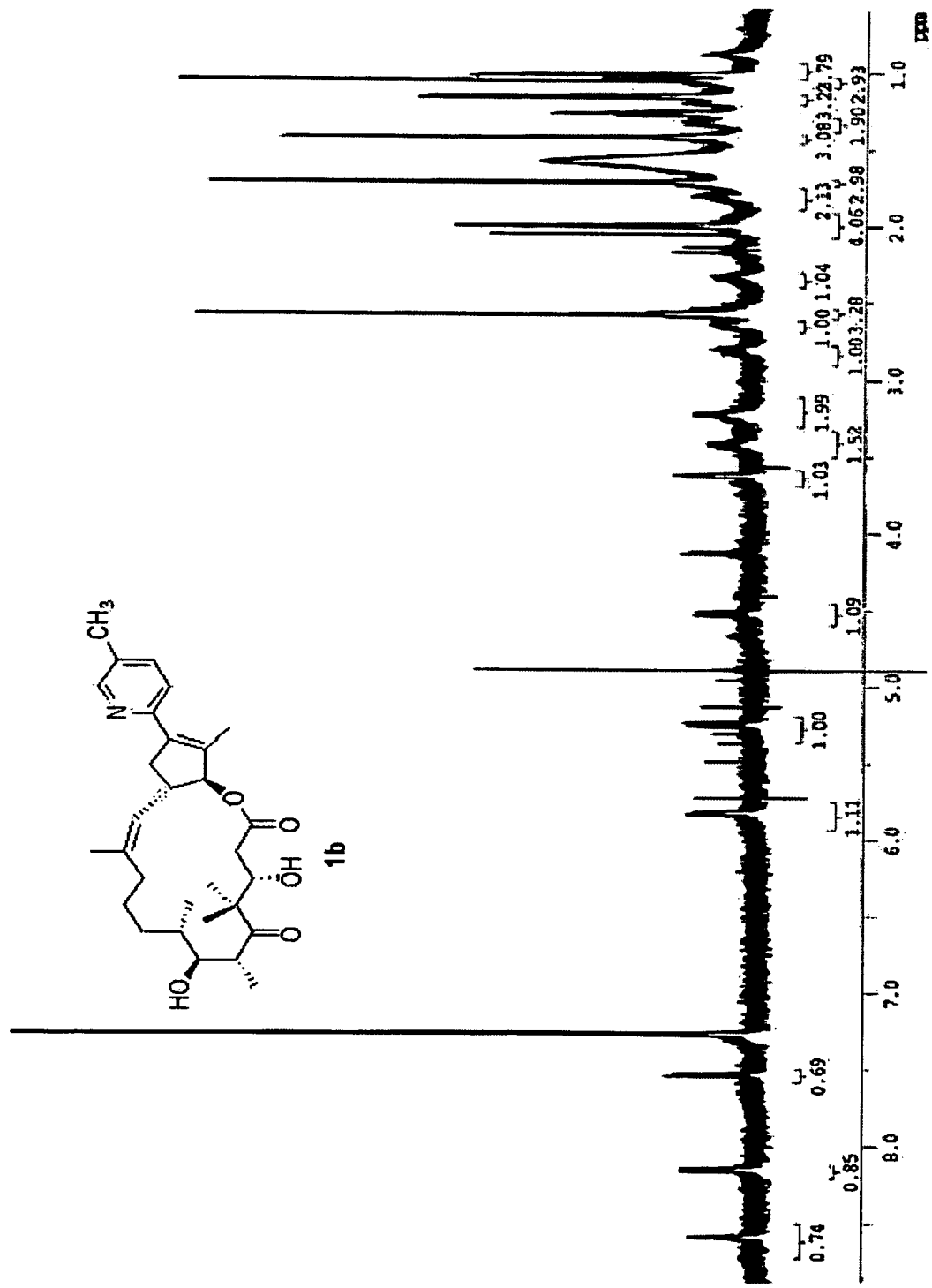
FIG. 18 shows the $^1$H NMR spectra for 1b.

FIG. 18 shows $^1$H NMR (500 MHz, CDCl$_3$) δ 8.60 (s, 1H), 8.16 (d, J=8.0 Hz, 1H), 7.54 (d, J=8.0 Hz, 1H), 5.84 (d, J=7.0 Hz, 1H), 5.25 (d, J=10.0 Hz, 1H), 4.53 (d, J=10.0 Hz, 1H), 3.64-3.62 (m, 1H), 3.47-3.40 (m, 2H), 3.26-3.21 (m, 2H), 2.81 (dd, J=2.5 Hz, 16.5 Hz, 1H), 2.65 (dd, J=10.5 Hz, 16.5 Hz, 1H), 2.59 (s, 3H), 2.38.2.31 (m, 1H), 2.0 (s overlapping with m, 5H), 1.84-1.79 (m, 2H), 1.72 (s, 3H), 1.42 (s, 3H), 1.35-1.31 (m, 2H), 1.16 (d, J=6.5 Hz, 3H), 1.06 (s, 3H), 1.02 (d, J=7.0 Hz, 3H); HRMS calcd for C$_{30}$H$_{43}$NO$_5$+H$^+$ 498.3219; found 498.3231 [M+H$^+$].

3,7-Dihydroxy-4,4,6,8,12-pentamethyl-5-oxo-tridec-12-enoic acid 2-methyl-3-(5-methyl-pyridin-2-yl)-5-styryl-cyclopent-2-enyl ester (35)

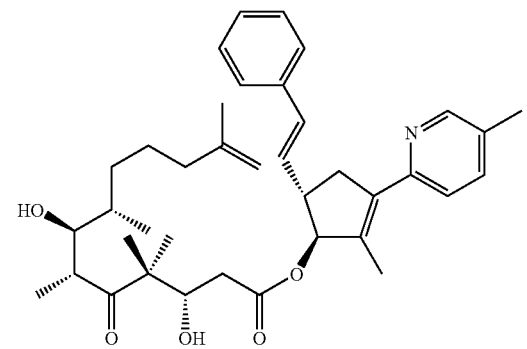

35

TLC $R_f$=0.61 (silica gel, 50% EtOAc/hexanes)

Figure 19:
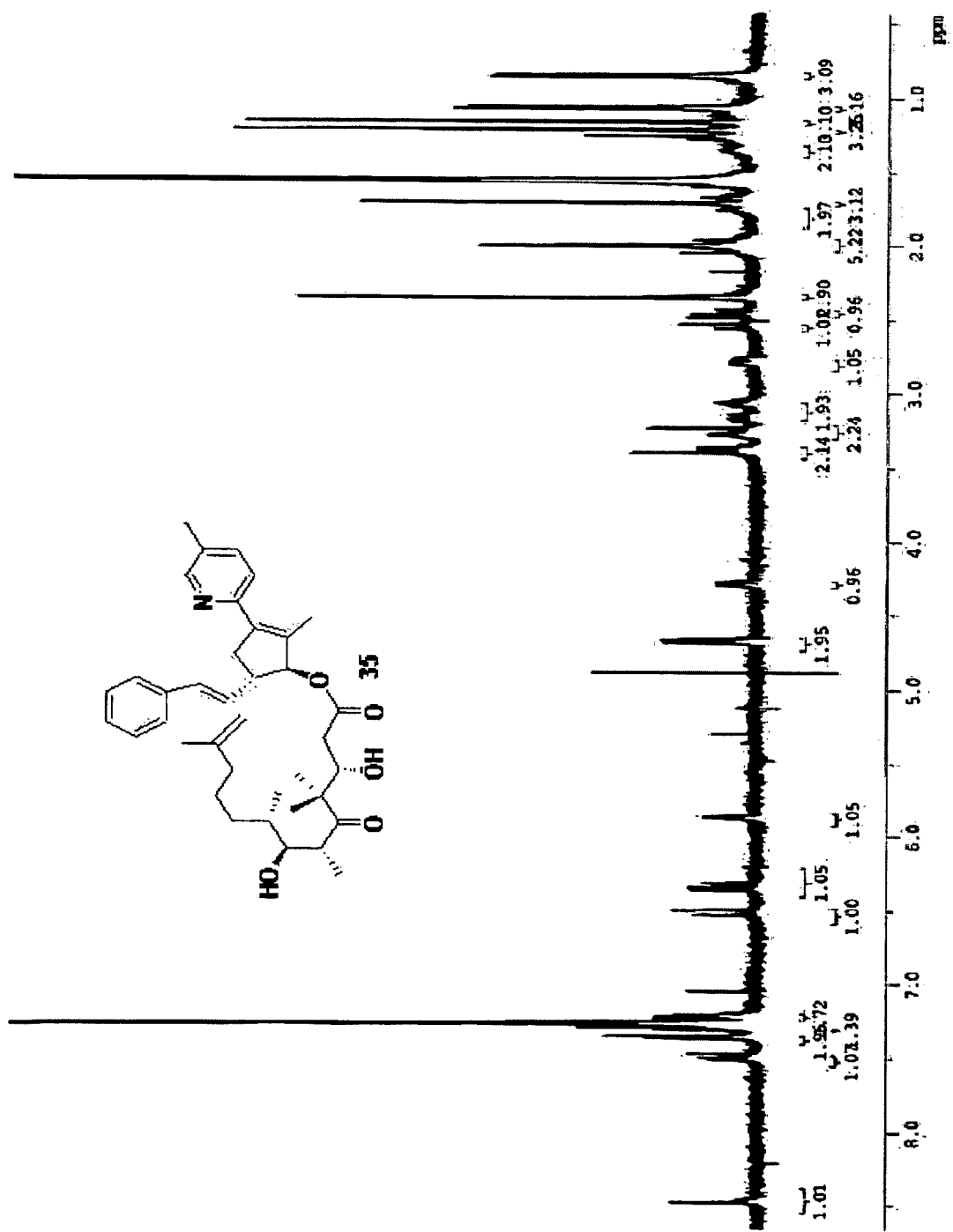
FIG. 19 shows the $^1$H NMR spectra for 35.

FIG. 19 shows $^1$H NMR (500 MHz, CDCl$_3$) δ 8.48 (d, J=2.0 Hz, 1H), 7.51 (dd, J=2.0 Hz, 8.0 Hz, 1H), 7.37-7.30 (m, 4H), 7.25-7.21 (m, 2H), 6.52 (d, J=16.0 Hz, 1H), 6.34 (dd, J=8.0 Hz, 16.0 Hz, 1H), 5.87 (d, J=4.5 Hz, 1H), 4.68 (d, J=9.0 Hz, 2H), 4.31-4.28 (m, 1H), 3.42-3.36 (m, 2H), 3.30-3.26 (m, 1H), 3.24 (d, J=4.0 Hz, 1H), 3.19-3.04 (m, 2H), 2.81-2.76 (m, 1H), 2.55 (dd, J=2.5 Hz, 16.0 Hz, 1H), 2.46 (dd, J=10.5 Hz, 16.0 Hz, 1H), 2.36 (s, 3H), 2.01 (s overlapping with m, 5H), 1.72 (m, 2H), 1.71 (s, 3H), 1.35 (m, 2H), 1.22 (s, 3H), 1.17 (s, 3H), 1.07 (d, J=7.0 Hz, 3H), 0.86 (d, J=7.0 Hz, 3H); HRMS calcd for $C_{38}H_{51}NO_5$+Na$^+$ 624.3665; found 624.3713 [M+Na$^+$].

Dimer 36

36

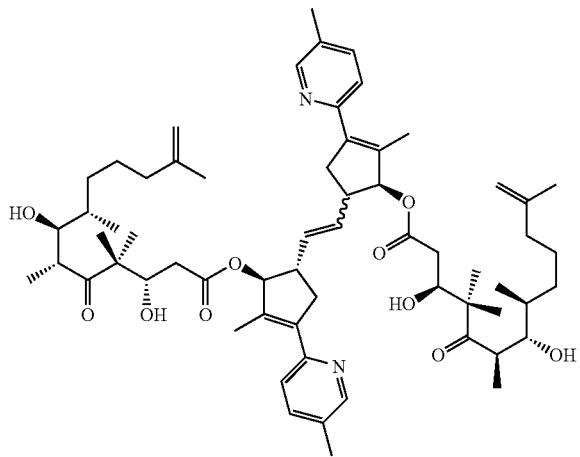

TLC $R_f$=0.37 (silica gel, 50% EtOAc/hexanes)

Figure 20:
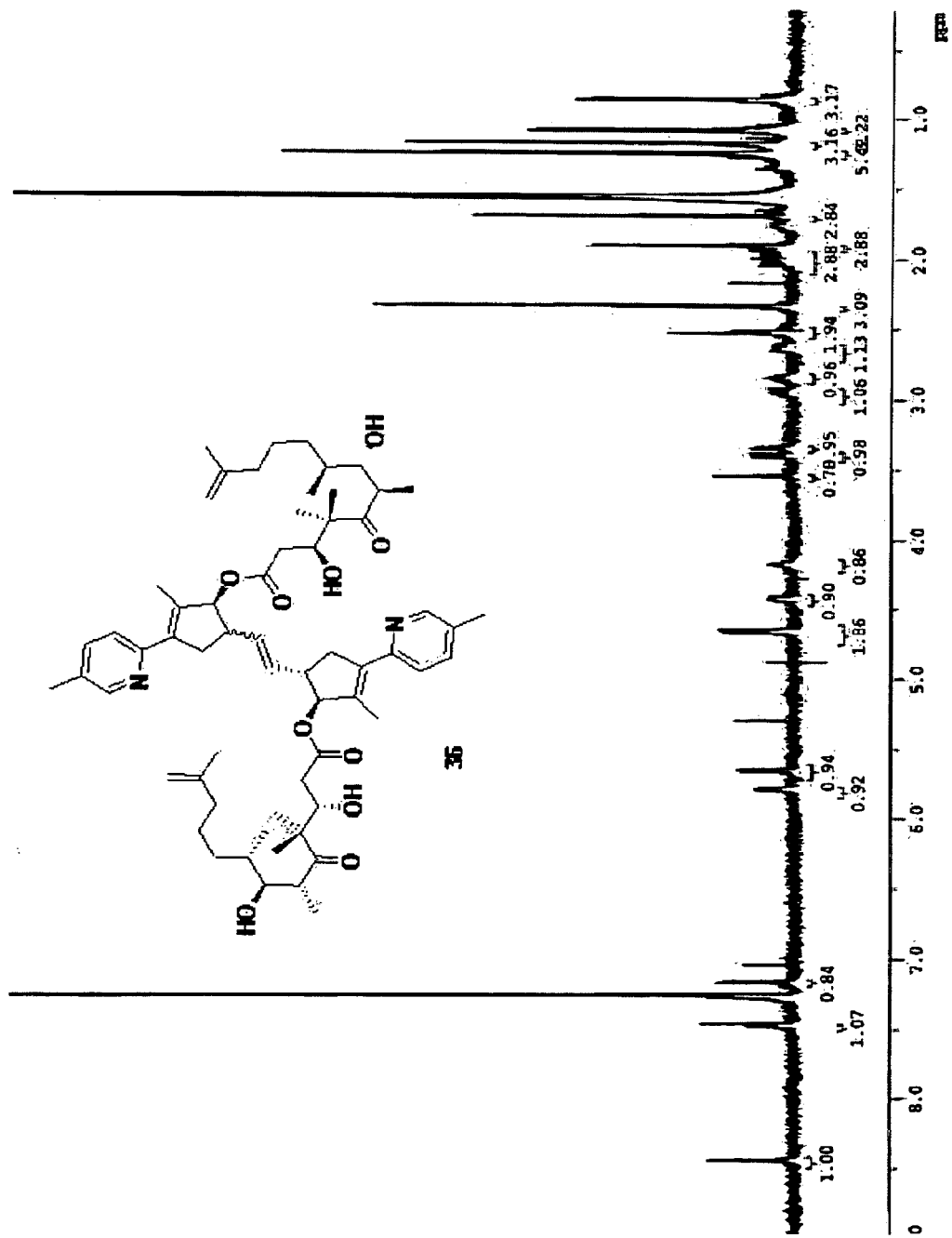
FIG. 20 shows the $^1$H NMR spectra for 36.

FIG. 20 shows $^1$H NMR (500 MHz, CDCl$_3$) δ 8.45 (d, J=2.0 Hz, 1H), 7.48 (dd, J=2.0 Hz, 8.0 Hz, 1H), 7.17 (d, J=8.0 Hz, 1H), 5.81-5.78 (m, 1H), 5.66 (dd, J=2.5 Hz, 5.5 Hz, 1H), 4.66 (d, J=7.5 Hz, 2H), 4.45-4.41 (m, 1H), 4.20-4.17 (m, 1H), 3.55 (s, 1H), 3.40 (d, J=9.0 Hz, 1H), 3.35 (dd, J=6.5 Hz, 13.5 Hz, 1H), 2.98-2.93 (m, 1H), 2.87-2.83 (m, 1H), 2.65-2.60 (m, 1H), 2.54-2.51 (m, 2H), 2.34 (s, 3H), 2.05-1.94 (m, 3H), 1.91 (s, 3H), 1.70 (s, 3H), 1.26 (s overlapping with m, 5H), 1.18 (s, 3H), 1.09 (d, J=7.0 Hz, 3H), 0.87 (d, J=7.0 Hz, 3H); HRMS calcd for $C_{62}H_{90}N_2O_{10}$+Na$^+$ 1045.6493 found 1045.6522 [M+Na$^+$].

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

REFERENCES

[1] M. C. Wani, H. L. Taylor, M. E. Wall, P. Coggon, A. T. McPhail, J. Am. Chem. Soc. 1971, 93, 2325.

[2] E. K. Rowinsky, Annu. Rev. Med. 1997, 48, 353.

[3] D. M. Bollag, P. A. McQueney, J. Zhu, O. Hensens, L. Koupal, J. Liesch, M. Goetz, E. Lazarides, C. M. Woods, Cancer Res. 1995, 55, 2325.

[4] R. J. Kowalski, P. Giannakakou, E. Hamel, J. Biol. Chem. 1997, 272, 2534.

[5] G. Hofle, N. Bedorf, K. Gerth, H. Reichenbach, Chem. Abstr. 1993, 120, 52841.

[6] K. Gerth, N. Bedorf, G. Hofle, H. Irschik, H. Reichenbach, J. Antibiot. 1996, 49, 560.

[7] K. H. Altmann, Curr. Pharm. Des. 2005, 11, 1595.

[8] D. S. Su, A. Balog, D. Meng, P. Bertinato, S. J. Danishefsky, Y. Zheng, T. C. Chou, L. He, S. B. Horwitz, Angew. Chem. 1997, 109, 2178; Angew. Chem. Int. Ed. Engl. 1997, 36, 2093.

[9] K. C. Nicolaou, F. Roschangar, D. Vourloumis, Angew. Chem. 1998, 110, 2120; Angew. Chem. Int. Ed. Engl. 1998, 37, 2014.

[10] M. Wartmann, K. H. Altmann, Curr. Med. Chem. Anticancer Agents 2002, 2, 123.

[11] D. W. Heinz, W. D. Schubert, G. Hofle, Angew. Chem. 2005, 117, 1324; Angew. Chem. Int. Ed. Engl. 2005, 44, 1298.

[12] E. B. Watkins, A. G. Chittiboyina, J. C. Jung, M. A. Avery, Curr. Pharm. Des. 2005, 11, 1615.

[13] A. Rivkin, T. C. Chou, S. J. Danishefsky, Angew. Chem. 2005, 117, 2890; Angew. Chem. Int. Ed. Engl. 2005, 44, 2838.

[14] K. C. Nicolaou, R. Scarpelli, B. Bollbuck, B. Werschkun, M. M. Pereira, M. Wartmann, K. H. Altmann, D. Zaharevitz, R. Gussio, P. Giannakakou, Chem. Biol. 2000, 7, 593.

[15] K. C. Nicolaou, D. Hepworth, N. P. King, M. R. Finlay, R. Scarpelli, M. M. Pereira, B. Bollbuck, A. Bigot, B. Werschkun, N. Winssinger, Chem. Eur. J. 2000, 6, 2783.

[16] J. H. Nettles, H. Li, B. Cornett, J. M. Krahn, J. P. Snyder, K. H. Downing, Science 2004, 305, 866.

[17] T. Carlomagno, M. J. Blommers, J. Meiler, W. Jahnke, T. Schupp, F. Petersen, D. Schinzer, K. H. Altmann, C. Griesinger, Angew. Chem. 2003, 115, 2615; Angew. Chem. Int. Ed. Engl. 2003, 42, 2511.

[18] K. H. Altmann, G. Bold, G. Caravatti, A. Florsheimer, V. Guagnano, M. Wartmann, Bioorg. Med. Chem. Lett. 2000, 10, 2765.

[19] G. Bold, S. Wojeik, G. Caravatti, R. Lindauer, C. Stierlin, J. Gertsch, M. Wartmann, K. H. Altmann, ChemMedChem 2006, 1, 37.

[20] K. C. Nicolaou, F. Sarabia, M. R. Finlay, S. Ninkovic, N. P. King, D. Vourloumis, Y. He, Chem. Eur. J. 1997, 3, 1971.

[21] H. J. Martin, P. Pojarliev, H. Kahlig, J. Mulzer, Chem. Eur. J. 2001, 7, 2261.

[22] J. Johnson, S. H. Kim, M. Bifano, J. DiMarco, C. Fairchild, J. Gougoutas, F. Lee, B. Long, J. Tokarski, G. Vite, Org. Lett. 2000, 2, 1537.

[23] K. C. Nicolaou, K. Namoto, A. Ritzen, T. Ulven, M. Shoji, J. Li, G. D'Amico, D. Liotta, C. T. French, M. Wartmann, K. H. Altmann, P. Giannakakou, J. Am. Chem. Soc. 2001, 123, 9313.

[24] T. C. Chou, H. Dong, A. Rivkin, F. Yoshimura, A. E. Gabarda, Y. S. Cho, W. P. Tong, S. J. Danishefsky, Angew. Chem. 2003, 115, 4910; Angew. Chem. Int. Ed. Engl. 2003, 42, 4762.

[25] J. P. Snyder, J. Nettles, D. C. Liotta, D. G. Kingston, G. Thota, PCT Int. Appl. WO 2006017761, 2006.

[26] K. C. Nicolaou, B. A. Pratt, S. Arseniyadis, M. Wartmann, A. O'Brate, P. Giannakakou, ChemMedChem 2006, 1, 41.

[27] F. Cachoux, T. Isarno, M. Wartmann, K. H. Altmann, Angew. Chem. 2005, 117, 7636; Angew. Chem. Int. Ed. Engl. 2005, 44, 7469.

[28] D. A. Evans, R. L. Dow, T. L. Shih, J. M. Takacs, R. Zahler, J. Am. Chem. Soc. 1990, 112, 5290.

[29] D. Schinzer, A. Bauer, J. Schieber, Chem. Eur. J. 1999, 5, 2492.

[30] K. C. Nicolaou, S. Ninkovic, F. Sarabia, D. Vourloumis, Y. He, H. Vallberg, M. R. Finlay, Z. Yang, J. Am. Chem. Soc. 1997, 119, 7974.

[31] J. A. Dale, H. S. Mosher, J. Am. Chem. Soc. 1973, 95, 512.

[32] I. Ohtani, T. Kusumi, Y. Kashman, H. Kakisawa, *J. Am. Chem. Soc.* 1991, 113, 4092.
[33] J. E. Parks, B. E. Wagner, R. H. Holm, *J. Organomet. Chem.* 1973, 56, 53.
[34] S. Cacchi, L. Caglioti, E. Cernia, *Synthesis* 1979, 1, 64.
[35] E. J. Corey, C. J. Helal, *Angew. Chem.* 1998, 110, 2092; *Angew. Chem. Int. Ed. Engl.* 1998, 37, 1986.
[36] D. F. Taber, L. J. Silverberg, *Tetrahedron Lett.* 1991, 32, 4227.
[37] J. Luche, A. Gemal, *J. Am. Chem. Soc.* 1979, 101, 5848.
[38] A. Gemal, J. Luche, *J. Am. Chem. Soc.* 1981, 103, 5454.
[39] W. J. Gensler, F. Johnson, A. Sloan, *J. Am. Chem. Soc.* 1960, 82, 6074.
[40] D. V. Patel, F. VanMiddlesworth, J. Donaubauer, G. P., C. Sih, *J. Am. Chem. Soc.* 1986, 108, 4603.
[41] K. A. Scheidt, H. Chen, B. C. Follows, S. R. Chemler, D. Coffey, W. R. Roush, *J. Org. Chem.* 1998, 63, 6436.
[42] M. M. Alhamadsheh, R. A. Hudson, L. M. Viranga Tillekeratne, *Org. Lett.* 2006, 8, 685.
[43] P. K. Jadhav, K. S. Bhat, P. T. Perumal, H. C. Brown, *J. Org. Chem.* 1986, 1, 432.
[44] W. J. Gensler, F. Johnson, A. Sloan, *J. Am. Chem. Soc.* 1960, 82, 6074.
[45] D. V. Patel, F. VanMiddlesworth, J. Donaubauer, G. P., C. Sih, *J. Am. Chem. Soc.* 1986, 108, 4603.
[46] D. Schinzer, A. Bauer, J. Schieber, *Chem. Eur. J. l* 1999, 5, 2492.
[47] K. C. Nicolaou, S. Ninkovic, F. Sarabia, D. Vourloumis, Y. He, H. Vallberg, M. R. Finlay, Z. Yang, *J. Am. Chem. Soc.* 1997, 119, 7974.

What is claimed is:

1. A composition comprising at least one epothilone analogue selected from the group consisting of:

an epothilone analogue represented by the following formula (1a) or a pharmaceutically acceptable salt, thereof:

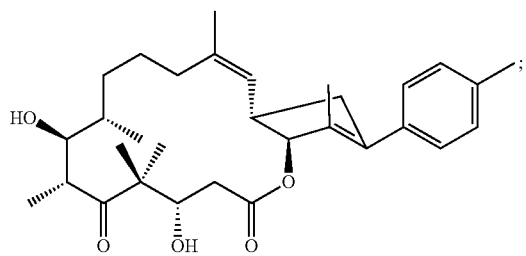

(1a)

an epothilone analogue represented by the following formula (1b) or a pharmaceutically acceptable salt, thereof:

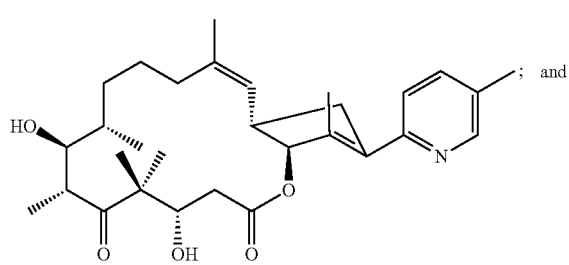

(1b)

a combination thereof.

2. The composition of claim 1, which comprises at least 50 wt. % of at least one epothilone analogue of claim 1, based on the total weight of the composition.

3. The composition of claim 1, further comprising a therapeutically effective amount of at least one epothilone analogue of claim 1; and a pharmaceutically acceptable carrier.

4. An epothilone analogue represented by the following general formula (1) or a pharmaceutically acceptable salt, thereof:

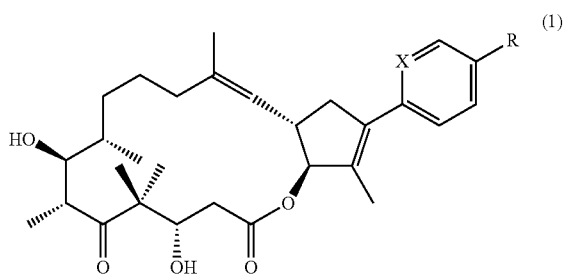

(1)

wherein:

R is a hydrogen atom or a methyl group; and

X is a carbon atom or a nitrogen atom.

5. The epothilone analogue according to claim 4, which is represented by the following formula (1a) or a pharmaceutically acceptable salt, thereof:

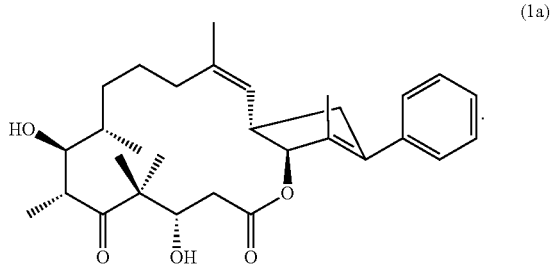

(1a)

6. The epothilone analogue according to claim 4, which is represented by the following formula (1b) or a pharmaceutically acceptable salt, thereof:

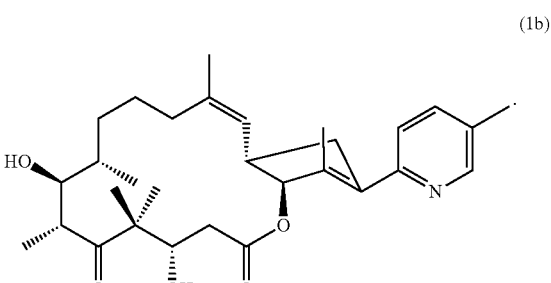

(1b)

* * * * *